US010421722B2

(12) United States Patent
Tu et al.

(10) Patent No.: US 10,421,722 B2
(45) Date of Patent: Sep. 24, 2019

(54) SULFUR-CONTAINING COMPOUNDS TARGETING VESICULAR ACETYLCHOLINE TRANSPORTER

(71) Applicants: Zhude Tu, St. Louis, MO (US); Zonghua Luo, St. Louis, MO (US); Hui Liu, St. Louis, MO (US); Hongjun Jin, St. Louis, MO (US); Stanley M. Parsons, Santa Barbara, CA (US)

(72) Inventors: Zhude Tu, St. Louis, MO (US); Zonghua Luo, St. Louis, MO (US); Hui Liu, St. Louis, MO (US); Hongjun Jin, St. Louis, MO (US); Stanley M. Parsons, Santa Barbara, CA (US)

(73) Assignees: Washington University, St. Louis, MO (US); The Regents of the University of California, Oakland, CA (US)

(*) Notice: Subject to any disclaimer, the term of this patent is extended or adjusted under 35 U.S.C. 154(b) by 0 days.

(21) Appl. No.: 15/620,263

(22) Filed: Jun. 12, 2017

(65) Prior Publication Data
US 2017/0355675 A1 Dec. 14, 2017

Related U.S. Application Data

(60) Provisional application No. 62/348,379, filed on Jun. 10, 2016.

(51) Int. Cl.
A61K 9/14 (2006.01)
C07D 211/32 (2006.01)
A61K 51/04 (2006.01)
A61B 6/03 (2006.01)
C07B 59/00 (2006.01)

(52) U.S. Cl.
CPC ............ C07D 211/32 (2013.01); A61B 6/037 (2013.01); A61K 51/0455 (2013.01); A61K 51/0497 (2013.01); C07B 59/001 (2013.01); A61K 51/0457 (2013.01); C07B 2200/05 (2013.01)

(58) Field of Classification Search
None
See application file for complete search history.

(56) References Cited

PUBLICATIONS

Agdeppa, E. D., et al., "Binding Characteristics of Radiofluorinated 6-Dialkylamino-2-Naphthylethylidene Derivatives as Positron Emission Tomography Imaging Probes for Beta-Amyloid Plaques in Alzheimer's Disease," 2001, J Neurosci, 21/24:RC189-189. 5 Pages.
Black, S., "The Biochemistry of Sulfur-Containing Compounds," 1963, Annu Rev Biochem, 32:399-418, 20 pages.
Bohnen, N. I., et al. "Cortical Cholinergic Function is More Severely Affected in Parkinsonian Dementia Than in Alzheimer Disease: An in vivo Positron Emission Tomographic Study," 2003, Arch Neurol, 60: 1745-1748. 4 Pages.
Catafau, A.M., et al. "Imaging Cortical Dopamine D1 Receptors Using [11C]NNC112 and Ketanserin Blockade of the 5-HT2A Receptors," 2010, J Cereb Blood Flow Metab, 30:985-993. 9 Pages.
Coyle, J., et al., "Alzheimer's Disease: a Disorder of Cortical Cholinergic Innervation," 1983, Science, 219/4589:1184-1190, 8 pages.
Davies, P., et al. (1976) "Selective Loss of Central Cholinergic Neurons in Alzheimer's Disease," 1976, The Lancet, 308:1403, 1 page.
Erickson, J.D., et al., "Molecular Analysis of Vesicular Amine Transporter Function and Targeting to Secretory Organelles," 2000, Faseb J. 14/15, 2450-2458, 6 pages.
Francis, P.T., et al., "The Cholinergic Hypothesis of Alzheimer's Disease: A Review of Progress," 1999, J Neurol, Neurosurg, Psychiatry, 66:137-147,11 pages.
Gage, H.D., et al. "Reproducibility of Repeated Measures of Cholinergic Terminal Density Using [18F]- Fluorobenzyltrozamicol and PET in the Rhesus Monkey Brain," 2000, J Nucl Med 41:2069-2076, 8 pages.
Gowrishankar, G., et al. "Investigation of 6-[18F]-Fluoromaltose as a Novel PET Tracer for Imaging Bacterial Infection," 2014, PLoS ONE 9/9, e107951, 6 pages.
Jin, H., et al., "Kinetics Modeling and Occupancy Studies of a Novel C-11 PET Tracer for VAChT in Nonhuman Primates," 2016, Nucl Med Biology, 43:131-139, 9 pages.
Jin, H., et al., "A Promising F-18 Labeled PET Radiotracer (-)-[18F]VAT for Assessing the VAChT in vivo," 2015, J Nucl Med 56:No. Supp. 3 4, Abstract Only, 1 page.
Khan, T., et al., "11C-Metomidate PET Imaging of Adrenocortical Cancer," 2003, Eur J Nuc. Med Mol Imaging, 30:403-410, 8 pages.
Kikuchi, T., et al., "PET Probes for Imaging Brain Acetylcholinesterase," 2013, J. Labelled Compd Radiopharm 56, 172-179, 8 pages.
Kilbourn, M. R., et al., "Mouse Brain Distribution of a Carbon-11 Labeled Vesamicol Derivative: Presynaptic Marker of Cholinergic Neurons," 1990, Life Sci, 47:1955-1963, 9 pages.
Li, J. et al., "Heteroaromatic and Aniline Derivatives of Piperidines as Potent Ligands for Vesicular Acetylcholine Transporter," 2013, J Med Chem, 56:6216-6233, 18 pages.
Liu, H., et al., "In vitro and ex vivo Characterization of (-)-TZ659 as a Ligand for Imaging the Vesicular Acetylcholine Transporter," 2015, European J Phamacology, 752:18-25, 8 pages.
Liu, H., et al., "Copper(II)-Catalyzed Single-Step Synthesis of Aryl Thiols from Aryl Halides and 1,2-Ethanedithiol," 2015, Adv Synth Catal, 357:2205-2212, 8 pages.
Luo, Z., et al., "Exploration of New Sulfur-Containing Analogues and in vivo Evaluation of a Lead F-18 PET Tracer for Imaging VAChT in Rodent and Nonhuman Primate," 2016, J Nucl Med, 57/Supp 2:160, Abstract Only, 1 page.
Luster, M., et al., "Clinical Value of 18F-Fluorodihydroxyphenylalanine Positron Emission Tomography/Computed Tomography (18F-DOPA PET/CT) for Detecting Pheochromocytoma," 2010, Eur J Nucl Med Mol Imaging, 37:484-493, 10 pages.

(Continued)

Primary Examiner — Michael G. Hartley
Assistant Examiner — Melissa J Perreira
(74) Attorney, Agent, or Firm — Stinson LLP

(57) ABSTRACT

The present invention generally relates to various compounds that are useful as vesicular acetylcholine transporter (VAChT) ligands. The invention further relates to methods of using these compounds and their radiolabeled analogs for the detection of neurodegenerative diseases including Parkinson's disease (PD), and Alzheimer's disease (AD).

20 Claims, 8 Drawing Sheets

(56) References Cited

PUBLICATIONS

Marien, M.R., et al., "Quantitative Autoradiography of Brain Binding Sites for the Vesicular Acetylcholine Transport Blocker 2-(4-Phenylpiperidino)Cyclohexanol (AH5183)," 1987, PNAS USA, 84:876-880. 5 pages.

Minn, H., et al., "Imaging of Adrenal Incidentalomas with PET Using 11C-Metomidate and 18F-FDG," 2004, J Nucl Med, 45:972-979, 8 pages.

Petrou, M., et al., "In vivo Imaging of Human Cholinergic Nerve Terminals with (-)-5-18F-Fluoroethoxybenzovesamicol: Biodistribution, Dosimetry, and Tracer Kinetic Analyses," 2014, J Nucl Med, 55:396-404, 10 pages.

Roghani, A., et al., "Molecular Cloning of a Putative Vesicular Transporter for Acetylcholine," 1994, PNAS USA, 91:10620-10624, 5 pages.

Rudd, J. H., et al., "Imaging Atherosclerotic Plaque Inflammation with [18F]-Fluorodeoxyglucose Positron Emission Tomography," 2002, Circulation, 105/23:2708-2711, 5 pages.

Shavnya, A., et al., "Palladium-Catalyzed Sulfination of Aryl and Heteroaryl Halides: Direct Access to Sulfones and Sulfonamides," 2013, Org Lett, 15:6226-6229, 4 pages.

Spencer, T. J., et al., "PET Study Examining Pharmacokinetics, Detection and Likeability, and Dopamine Transporter Receptor Occupancy of Short- and Long-Acting Oral Methylphenidate," 2006, Am J Psychiatry, 163:387-395, 9 pages.

Tu, Z., et al., "Synthesis and Biological Characterization of a Promising F-18 PET Tracer for Vesicular Acetylcholine Transporter," 2015, Bioorg & Med Chem, 23:4699-4709,11 pages.

Tu, Z. et al., "Synthesis and in vitro and in vivo Evaluation of 18F-Labeled Positron Emission Tomography (PET) Ligands for Imaging the Vesicular Acetylcholine Transporter," 2009, J Med Chem, 52/5:1358-1369, 31 pages.

Tu, Z. et al., "Fluorine-18-Labeled Benzamide Analogues for Imaging the Sigma-2 Receptor Status of Solid Tumors with Positron Emission Tomography," 2007, J Med Chem, 50:3194-3204, 11 pages.

Tu, Z., et al., "Carbon-11 Labeled Sigma-2 Receptor Ligands for Imaging Breast Cancer," 2005, Nucl Med Biol, 32:423-430., 8 pages.

Wang, W., et al., "Synthesis and in vitro Biological Evaluation of Carbonyl Group-Containing analogues for Sigma 1 Receptors," 2011, J Med Chem, 54:5362-5372, 11 pages.

Weihe, E., et al., "Visualization of the Vesicular Acetylcholine Transporter in Cholinergic Nerve Terminals and its Targeting to a Specific Population of Small Synaptic Vesicles," 1996, PNAS, 93:3547-3552, 6 pages.

Weinstein, E.A., et al., "Imaging Enterobacteriaceae Infection in vivo with 18F-Fluorodeoxysorbitol Positron Emission Tomography," 2014, Sci Trans Med, 6:1-20, 20 pages.

Widén, L., et al., "Positron Emission Tomographic Studies of Central Cholinergic Nerve Terminals," 1992, Neurosci Lett, 136:1-4, 4 pages.

Yue, X., et al., "Automated Production of [18F]VAT Suitable for Clinical PET Study of Vesicular Acetylcholine Transporter," 2016, Appl Radiat Isot, 107:40-46,16 pages.

Yung-Chi, C., et al., "Relationship Between the Inhibition Constant (Ki) and the Concentration of Inhibitor which Causes 50 Percent Inhibition (I50) of an Enzymatic Reaction," 1973, Biochem Pharmacol, 22:3099-3108, 10 pages.

Zea-Ponce, Y., et al., "Synthesis and in vitro Evaluation of New Benzovesamicol Analogues as Potential Imaging Probes for the Vesicular Acetylcholine Transporter," 2005, Bioorg Med Chem, 13:745-753, 9 pages.

A

B $(-)-[^{11}C]3$

C

D $(-)-[^{18}F]9a$

SULFUR-CONTAINING COMPOUNDS TARGETING VESICULAR ACETYLCHOLINE TRANSPORTER

REFERENCE TO RELATED APPLICATIONS

This application claims benefit of U.S. provisional application Ser. No. 62/348,379 filed Jun. 10, 2016, the entire disclosure of which is incorporated herein by reference.

GOVERNMENT LICENSE RIGHTS

This invention was made with Government support under Grant Numbers NS061025, NS075527, and MH092797 awarded by the National Institutes of Health and DE-SC0012737 awarded by the Department of Energy. The Government has certain rights in the invention.

FIELD OF THE INVENTION

The present invention generally relates to various compounds that are useful as vesicular acetylcholine transporter (VAChT) ligands. The invention further relates to methods of using these compounds and their radiolabeled analogs for the detection of neurodegenerative diseases including Parkinson's disease (PD), and Alzheimer's disease (AD).

BACKGROUND OF THE INVENTION

Dysfunction of the cholinergic system and loss of synaptic pruning in the brain could induce progressive diminution in cognitive function, which is the main feature of neurodegenerative diseases, such as Alzheimer's disease[1-3], and Parkinson's disease.[4] Acetylcholine (ACh) is the primary neurotransmitter of cholinergic neurons in the central nervous system (CNS). Vesicular acetylcholine transporter (VAChT) is a neurotransmitter transporter which is responsible for loading ACh into secretory organelles in neurons making acetylcholine available for secretion.[5,6] It is a reliable biomarker for assessing the status of cholinergic neurons in the central nervous system.[7,8] Therefore, in vivo measurement of VAChT could provide a valuable understanding of the pathophysiology and diagnoses of these neurological disorders.

Positron emission tomography (PET) is a molecular imaging technique that produces a three-dimensional image of functional processes in the body and it is a sensitive and non-invasive method that can determine the biological activities of soft tissues. Currently, PET technique is used heavily in clinical oncology[9-11], neuroimaging[12,13], cardiology[14], infectious[15,16], and pharmacokinetics[17].

There remains a need for improved diagnostic tools for assessing cholinergic neurons in vivo, including the ability to monitor the efficacy of cholinergic therapies in living patients. The development of suitable PET tracers to assess the loss of cholinergic neurons could provide useful information for monitoring the efficacy of cholinergic therapies in neurodegenerative diseases on a living subject.[18] Vesicular acetylcholine transporter (VAChT) provides a reliable biomarker for cholinergic function in neurodegenerative diseases.

Currently, a number of radiotracers which were developed based on the structure of (−)-Vesamicol have been evaluated as VAChT imaging agents, such as (−)-[$^{18}$F]FMV,[19] (+)-[$^{18}$F]FBT,[20] (−)-[$^{11}$C]mABV,[21] (−)-[$^{18}$F]FEOBV,[22] (−)-[$^{11}$C]TZ659,[23] and (−)-[$^{18}$F]VAT.[24] However, most of the radiotracers show unfavorable properties when applied to preclinical studies, such as poor extraction from blood, slow brain kinetics, and fast metabolism. Recently, (−)-[$^{18}$F]FEOBV and (−)-[$^{18}$F]VAT were reported for VAChT imaging in human studies.[22,25] (−)-[$^{18}$F]FEOBV offers advantages over single-photon emission computed tomography (SPECT) ligands for both preclinical and clinical imaging of cholinergic loss.[22] (−)-[$^{18}$F]VAT, which was developed and completed with rodents and NHP pre-clinical investigations by the inventors, was recently approved for the clinical research in human subjects.

A good radiotracer needs optimal pharmacokinetics before it can be applied on human subject. Thus, there remains a need for suitable VAChT PET tracers with improved pharmacokinetics.

BRIEF SUMMARY OF THE INVENTION

In various aspects, the present invention is directed to compounds that function as ligands for VAChT as well as radiolabeled analogs of these compounds that are useful for diagnosing or monitoring neurodegeneration in a subject. For example, ligands for VAChT of the present invention include compounds of Formula I, or a salt thereof:

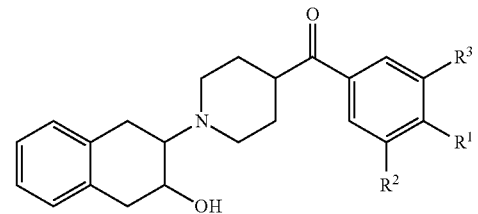

(I)

wherein $R^1$, $R^2$, and $R^3$ are each independently hydrogen, $C_1$-$C_6$ alkyl, or

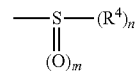

and at least one of $R^1$, $R^2$, and $R^3$ is

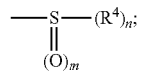

$R^4$ is a substituted or unsubstituted $C_1$-$C_6$ alkyl, or substituted or unsubstituted amino;

m is 0, 1 or 2; and n is 0 or 1.

Further aspects of the present invention are directed to compounds of Formula I that are radiolabeled, for example, with an isotope useful for positron emission tomography. In other aspects, the present invention is directed to methods for diagnosing or monitoring neurodegeneration in a human subject comprising administering a radiolabeled compound of Formula I to the human subject; and imaging the subject's brain by positron emission tomography Other objects and features will be in part apparent and in part pointed out hereinafter.

DETAILED DESCRIPTION OF THE INVENTION

Figure 1:
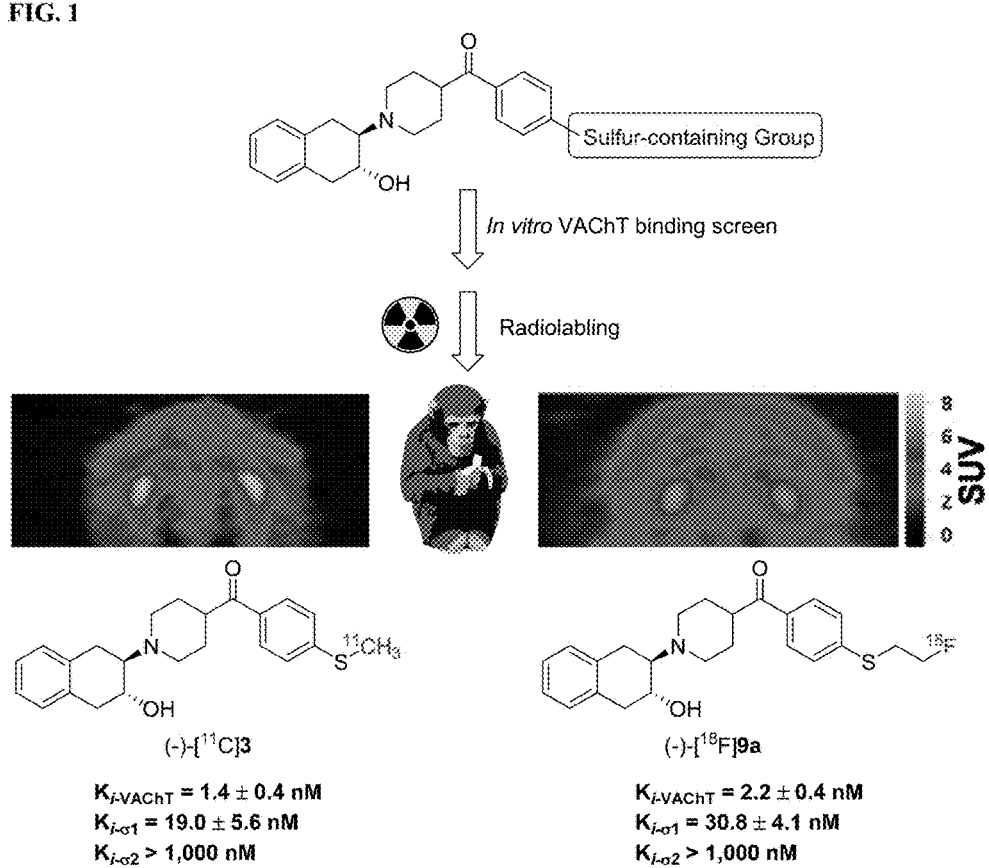
FIG. 1 depicts the overall experimental scheme of deriving sulfur containing compounds, radiolabeling them, and measuring their localization in non-human primates.

Generally, the present invention is directed to compounds that are useful vesicular acetylcholine transporter (VAChT) ligands. Radiolabeled analogs of the compounds described herein are useful for certain diagnostic methods for neurodegenerative diseases or to monitor treatment in patients.

The present invention is also directed to the VAChT ligands that are radiolabeled with radionuclides such as carbon-11 and/or fluorine-18 to serve as imaging agents (e.g., positron emission tomography (PET) imaging agents) for quantifying VAChT in the brain. The in vivo quantification of VAChT in patients is useful not only for diagnosing neurodegenerative diseases such as Parkinson's Disease and Alzheimer's Disease, but also for monitoring disease progression or treatment efficacy.

In accordance with various aspects of the present invention, compounds useful as VAChT ligands comprise compounds of Formula I, or a salt thereof:

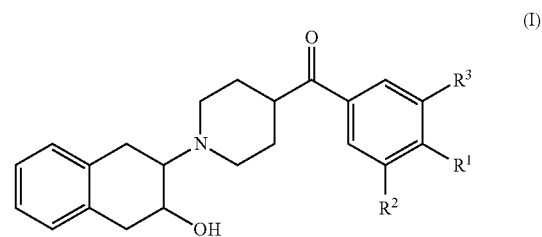

(I)

wherein $R^1$, $R^2$, and $R^3$ are each independently hydrogen, $C_1$-$C_6$ alkyl, or

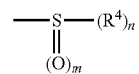

and at least one of $R^1$, $R^2$, and $R^3$ is

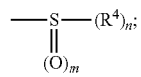

$R^4$ is a substituted or unsubstituted $C_1$-$C_6$ alkyl, substituted or unsubstituted amino;
m is 0, 1 or 2; and
n is 0 or 1.

In various embodiments, at least two of $R^1$, $R^2$, and $R^3$ are hydrogen. In some embodiments, $R^2$ and $R^3$ are each hydrogen.

In various embodiments, $R^4$ is a $C_1$-$C_6$ alkyl, substituted or unsubstituted $C_1$-$C_6$ alkylamino, substituted or unsubstituted $C_1$-$C_6$ haloalkyl. In further embodiments, $R^4$ is a methyl, ethyl, propyl, butyl, fluoroethyl, fluoropropyl, methylamino, ethylamino, methylamino, ethylamino, fluoroethylamino, or fluoropropylamino.

In various embodiments, the compounds of Formula I include compounds of the structure of Formula II, or a salt thereof:

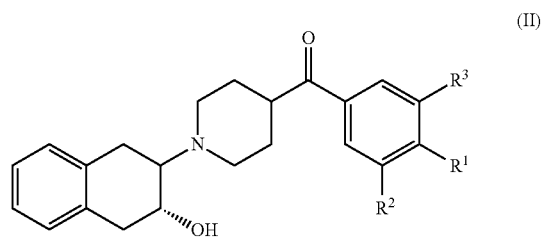

(II)

wherein $R^1$, $R^2$, and $R^3$ are as described above.

Compounds of Formula II can further include compounds of the structure of Formula II-B:

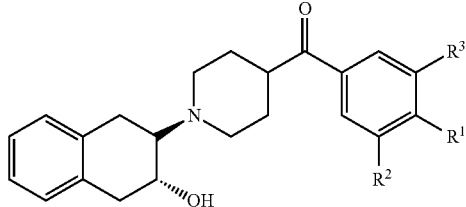
(II-B)

wherein R¹, R², and R³ are as described above.

In various embodiments, the compound of Formula I is selected from the group consisting of:

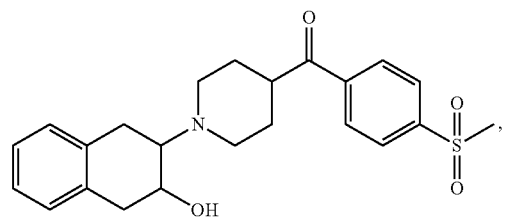

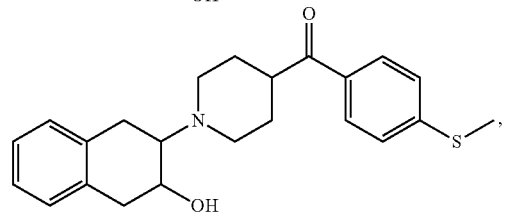

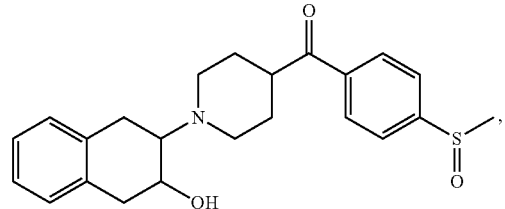

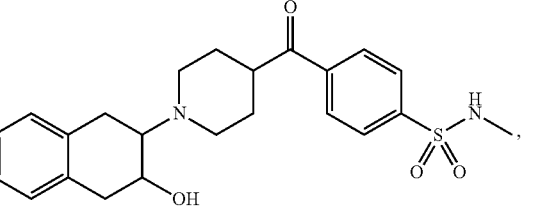

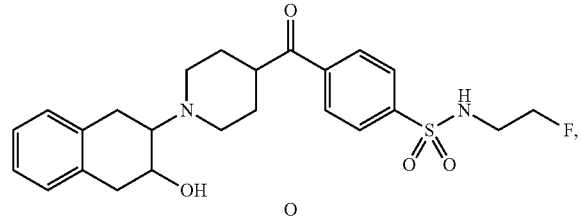

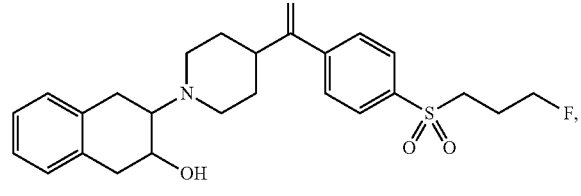

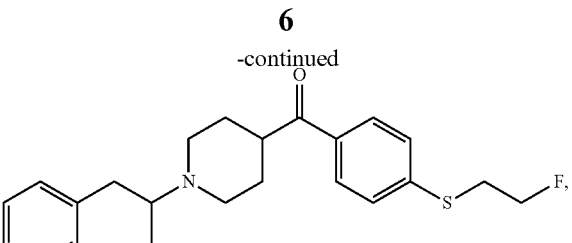

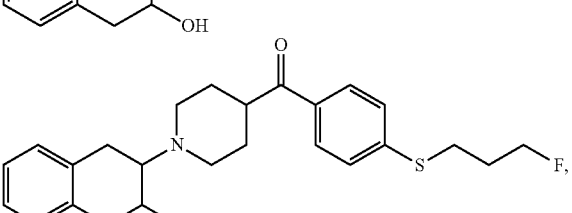

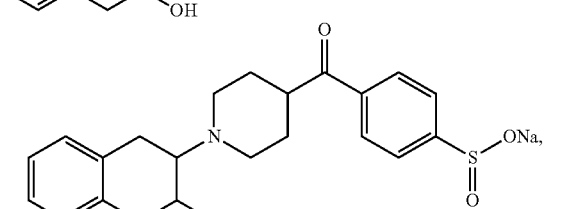

stereoisomers or salts thereof, and mixtures thereof.

In some embodiments the compound of Formula I is selected from the group consisting of:

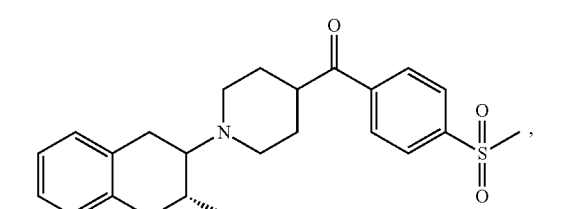

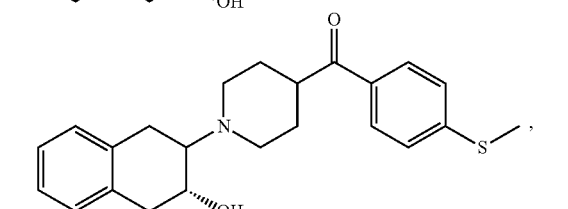

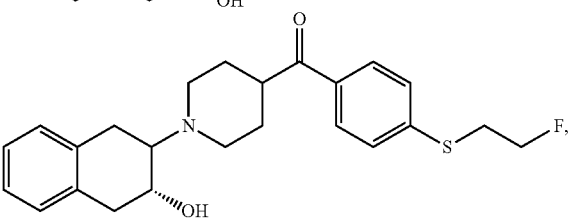

stereoisomers or salts thereof, and mixtures thereof.

In certain embodiments the compound of Formula I is selected from the group consisting of:

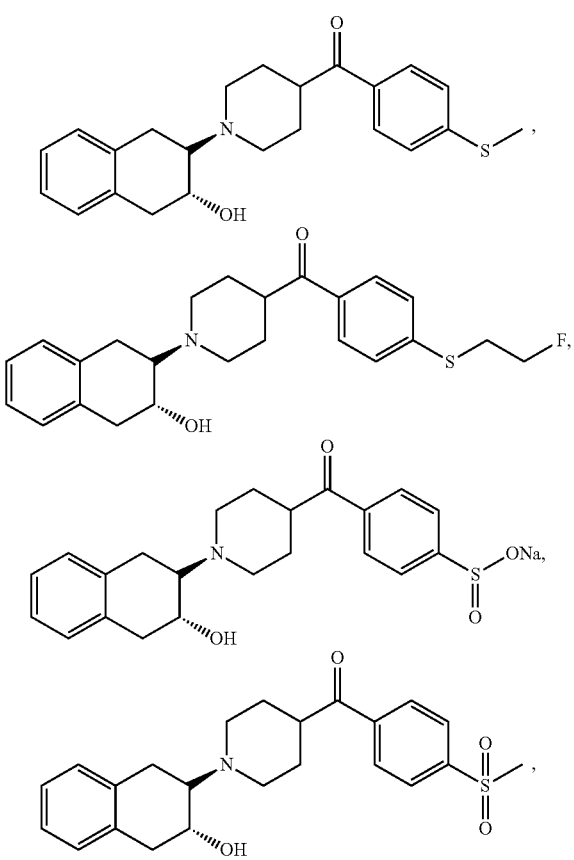

salts thereof, and mixtures thereof.

As noted, the compounds of the present invention possess binding affinity to VAChT which is useful for certain diagnostic and monitoring methods for neurodegenerative diseases characterized by loss of cholinergic neurons, such as Alzheimer's Disease and Parkinson's Disease. One diagnostic method that is suitable for use with the VAChT ligands of the present invention is positron emission tomography (PET). PET is known in the art of nuclear medicine imaging as a non-invasive imaging modality that can provide functional information of a living subject at the molecular and cellular level. PET utilizes biologically active molecules in micromolar or nanomolar concentrations that have been labeled with short-lived positron emitting isotopes. The physical characteristics of the isotopes and the molecular specificity of labeled molecules, combined with the high detection efficacy of modern PET scanners provides a sensitivity for in vivo measurements of indicator concentrations that is several orders of magnitude higher than with other imaging techniques.

In order to make measurements with PET, a biologically active tracer molecule labeled with a positron-emitting isotope is administered to a subject, for example, intravenously, orally, or by inhalation. The subject is then scanned, and axial tomographic slices of regional cerebral tracer accumulation are obtained. This tracer accumulation can be related to cerebral metabolism, blood flow, or binding site concentrations by appropriate mathematical models. Thus, by using a small molecular PET radiotracer which has high affinity and selectivity to VAChT, the status of cholinergic neurons in the brain can be quantified. This approach not only improves the diagnostic accuracy of neurodegenerative diseases, but also provides a tool to monitor the progression of the disease and the efficacy of the treatment, and improve the understanding of disease progression.

Accordingly, any of the compounds of the present invention described herein, including those represented by Formulas I, II, and IIB can be labeled with a radioactive isotope (e.g., synthetic radioactive isotopes) including, for example, carbon-11, nitrogen-13, oxygen-15, fluorine-18, bromine-76, iodine-123, and iodine-125 to serve as tracers for quantifying VAChT in the brain. In various embodiments, the compounds of Formulas I, II, and IIB are labeled with a radioactive isotope selected from the group consisting of carbon-11, fluorine-18, iodine-123, and iodine-125. Methods known in the art for radiolabeling the compounds of the present invention may be used.

In some embodiments, the radiolabeled compounds embodied by this invention can be selected from the group consisting of:

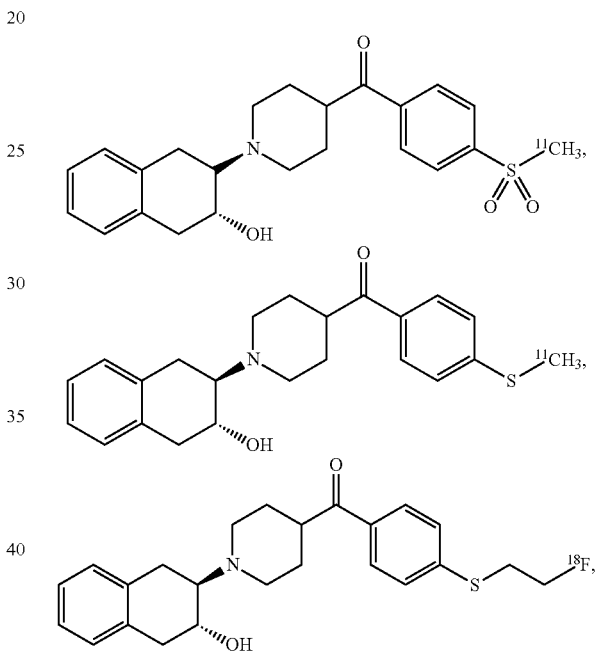

salts thereof, and mixtures thereof

The present invention is also directed to various pharmaceutical compositions comprising one or more of radiolabeled compounds of Formulas I, II, and/or IIB as defined herein. In various embodiments, the pharmaceutical composition comprises from about 0.001 mg to about 10 g of a compound of Formulas I, II, and/or IIB and at least about 10 wt. %, at least about 25 wt. %, at least about 50 wt. %, at least about 75 wt. %, at least about 90 wt. %, or at least about 95 wt. % of the compound in the pharmaceutical composition is radiolabeled. The pharmaceutical compositions can also contain one or more excipients.

The compounds of present invention may be formulated in a suitable pharmaceutical delivery medium or vehicle. In various embodiments, the pharmaceutical composition comprises an injectable comprising a compound of the present invention. In other embodiments, the pharmaceutical delivery medium comprises an oral vehicle comprising a compound of the present invention (e.g., capsule, pill, liquid, suspension, etc.).

Further, in accordance with the present invention, methods for diagnosing or monitoring cholinergic neurodegeneration are provided. In various embodiments, the method for diagnosing or monitoring neurodegeneration in a human subject comprises administering a radiolabeled compound of Formula I or pharmaceutical composition comprising a radiolabeled compound of Formula I to the human subject; and imaging the subject's brain by positron emission tomography.

Having described the invention in detail, it will be apparent that modifications and variations are possible without departing from the scope of the invention defined in the appended claims.

EXAMPLES

The following non-limiting examples are provided to further illustrate the present invention.

Summary of Examples

Herein, the general strategy and interpretation of the experiments that follow is laid out. Compounds named will be described in more detail in the following examples. An overview of the experimental procedure is depicted in FIG. 1.

Vesicular acetylcholine transporter (VAChT) provides a reliable biomarker for cholinergic function in neurodegenerative diseases. New sulfur-containing compounds were synthesized using mild reaction conditions and potential compounds were resolved via chiral HPLC on a semi-preparative Chiralcel OD column. (−)-[$^{18}$F]9a was synthesized by alkylation of the corresponding thiophenol with 2-[$^{18}$F]fluoroethyl tosylate which was prepared by reacting [$^{18}$F]/fluoride with ethylene ditosylate. Autoradiography studies were performed using the brain slices of Sprague-Dawley rats (250-400 g) 60 min post injection of the radiotracer. MicroPET studies were performed using male cynomolgus monkeys (6-8 kg) with a MicroPET Focus 220 scanner.

16 new sulfur-containing compounds were synthesized with yields of 10-66% and in vitro binding assays showed that (−)-9a had a high binding affinity to VAChT (2.2 nM). (−)-[$^{18}$F]9a was prepared with high chemical (>95%) and radiochemical (>95%) purity as well as high specific activity (>55 GBq/μmol, EOS). Ex vivo autoradiography and in vivo MicroPET imaging indicated that (−)-[$^{18}$F]9a displayed a high uptake in the VAChT enriched striatum versus other brain regions including cerebellum, cortex, temporal, middle brain, hippocampus, and thalamus. The radioactivity accumulation (standardized uptake value, SUV) of (−)-[$^{18}$F]9a in striatum reached maximum with a value of 5.2 at 6 min post injection, and washed out quickly from the peak value.

The new sulfur-containing analogues display high potency for VAChT. The lead radiotracer (−)-[$^{18}$F]9a has the potential to be a promising radiotracer for in vivo quantifying the expression of VAChT with PET.

The inventors explored a series of new analogues by incorporating diverse sulfur-containing groups into the lead pharmacophore structure for VAChT and performed in vitro biological activity determination. Among these new analogues, several compounds have high potency (Ki<15 nM for VAChT). The potent racemic compounds were resolved to obtain their enantiomeric pure minus (−) and plus (+) isomer. The potent isomer (−)-9a was selected for radiolabeling to afford (−)-[18F]9a. The initial evaluation of (−)-[18F]9a were performed in rodents and nonhuman primates via Ex vivo autoradiography and in vivo PET imaging studies, suggesting that (−)-[18F]9a having high specific binding to VAChT in vivo at striatum and suitable washout kinetics from the brain. These data suggested that (−)-[18F]9a and its analogues may have improving pharmacological properties compared to current reported compounds and these sulfur containing analogues may have high potential to be a suitable PET radiotracer for in vivo assessment of VAChT level, which will offer new methodology to assess the cognitive dysfunction for dementia including AD, PD, Huntington disease and others.

The new tracer (−)-[18F]9a, or the C-11 labeled tracer displayed highly binding affinities of 2.2 nM. The ex vivo autoradiography and in vivo MicroPET imaging indicated that (−)-[18F]9a has the highest uptake (SUV) in the VAChT enriched striatum. The striatal uptake of (−)-[18F]9a quickly reached peak and the clearance kinetics was improved compared to reported PET tracers for VAChT. In addition, some of these new analogues. These promising initial in vitro and in vivo results suggested (−)-[18F]9a and its analogues may have high potential to be a PET radiotracer for clinical use. Some of these compounds also have high affinity for sigma receptors, which provide the potential use as therapeutic or imaging tracers targeting on Sigma receptors.

In all, a series of sulfur-containing compounds targeting VAChT were successfully synthesized, including thioether, sulfoxide, sulfone, and sulfamide. In vitro binding studies suggested that all the ligands showed good binding affinities to VAChT, especially compounds (−)-3 (1.4 nM), (−)-9a (2.2 nM), and (−)-9b (1.4 nM). (−)-3 and (−)-9a were chosen to perform the 11C and 18F radiolabeling for further evaluation in rodents and nonhuman primates because of their high VAChT binding affinities and moderate selectivity to σ1 receptor. Ex vivo autoradiography studies in rodents and MicroPET studies in nonhuman primates suggested that both (−)-[11C]3 and (−)-[18F]9a have a high accumulation in the VAChT enriched striatum. The uptake of (−)-[11C]3 and (−)-[18F]9a in striatum reached maximum SUV of 4.0 at 10 min and 6.3 at 6 min post injection, respectively. After reaching the peak, the tracers were washed out quickly, which demonstrated that the introduction of sulfur to the tracer could improve the brain kinetic property.

In sum, vesicular acetylcholine transporter (VAChT) provides a reliable biomarker for cholinergic neurons function in neurodegenerative diseases. The inventors designed and synthesized a series of sulfur-containing compounds, including thioether, sulfoxide, sulfone, and sulfamide. In vitro VAChT binding studies found two leading potent compounds (−)-3 and (−)-9a displayed high binding affinities to VAChT of 1.4 nM and 2.2 nM. (−)-[11C]3 was radiolabeled from the precursor (−)-8 using [11C]CH3I with radiochemical yield of 50-60% and specific activities of >74 GBq/μmol (decay corrected to end of synthesis, EOS). (−)-[18F]9a was accomplished from the precursor (−)-8 using [18F]fluoroethyl tosylate with radiochemical yield of 20-30% and specific activities of >55 GBq/μmol (EOS). The ex vivo rat autoradiography images and in vivo non-human primates (NHP) MicroPET results showed both (−)-[11C]3 and (−)-[18F]9a have a high accumulation in the VAChT enriched striatum. The tissue activity curves revealed both (−)-[11C]3 and (−)-[18F]9a have highest accumulation in striatum and washed out quickly. Our initial results suggested that (−)-[11C]3 and (−)-[18F]9a have good potential to be PET radiotracers for in vivo quantifying of VAChT General Information:

Abbreviations:

VAChT, vesicular acetylcholine transporter; ACh, acetylcholine; CNS, central nervous system; PET, positron emission tomography; SPECT, single-photon emission computed tomography; NHP, nonhuman primate; TBAB, tetrabutylammonium bromide; DMF, N,N-dimethylformamide; NCS, N-chlorosuccinimide; DMSO, dimethyl sulfoxide; SUV, standardized uptake value; MRI, magnetic resonance imaging; TLC, thin-layer chromatography; EOB, end-of-bombardment; VOI, volume of interest.

General Methods and Supplies:

Commercially available starting materials, reagents, and solvents were used as received. Unless otherwise indicated, all reactions were conducted in oven dried glassware. In general, anhydrous reactions were performed under nitrogen. Yields refer to chromatographically, unless otherwise stated. Reactions were monitored by thin-layer chromatography (TLC) carried out on precoated glass plates of silica gel (0.25 mm) 60 $F_{254}$ from EMD Chemicals Inc. Visualization was accomplished with ultraviolet light (UV 254 nm), or by shaking the plate in a sealed jar containing silica gel and Iodine. Flash column chromatography was performed using Silica Flash® P60 silica gel (40-63 μm) from Silicycle. All work-up and purification procedures were carried out with reagent grade solvents in air. $^1$H NMR spectra were recorded on Varian 400 MHz and 300 MHz instruments. Chemical shifts were reported in parts per million (ppm) and were calibrated using residual undeuterated solvent as an internal reference (CDCl$_3$: δ 7.26 ppm; MeOH-d4: δ 3.31 ppm; DMSO-d6: δ 2.50 ppm). Data are reported as follows: chemical shift, multiplicity, coupling constants (Hz), and integration. The following abbreviations or combinations thereof were used to explain the multiplicities: s=singlet, d=doublet, t=triplet, q=quartet, pent=pentet, sext=sextet, sept=septet, m=multiplet, at =apparent triplet, aq=apparent quartet, b=broad. The SpectraSystem was used for both analytical and semi-preparative HPLC. A Chiralcel OD normal phase HPLC column was used to resolve enantiomers. The specific optical rotation was determined on an automatic polarimeter (Autopol 111, Rudolph Research, Flanders, N.J.).

General procedure of producing radioisotopes. [$^{11}$C]CH$_3$I was produced from the JSW BC-16/8 cyclotron as previously described.[31] [$^{18}$F]Fluoride was produced from a RDS111 cyclotron (Siemens/CTI Molecular Imaging, Knoxville, Tenn.) by $^{18}$O(p, n)$^{18}$F reaction through proton irradiation of enriched $^{18}$O water (95%). [$^{18}$F]Fluoride was firstly passed through an ion-exchange resin and then eluted using 0.02 M potassium carbonate solution.

General procedure of oxalates. A solution of oxalic acid in ethyl acetate (0.3 M, 1 eq) was added slowly into a solution of free base in dichloromethane (0.06 M, 1 eq) in a vial equipped with a magnetic stir bar. The mixture was stirred for 5 h at room temperature and filtered to afford the oxalate as a white solid.

Example 1: Synthesis of Sulfur-Containing VAChT Ligands

Figure 2:
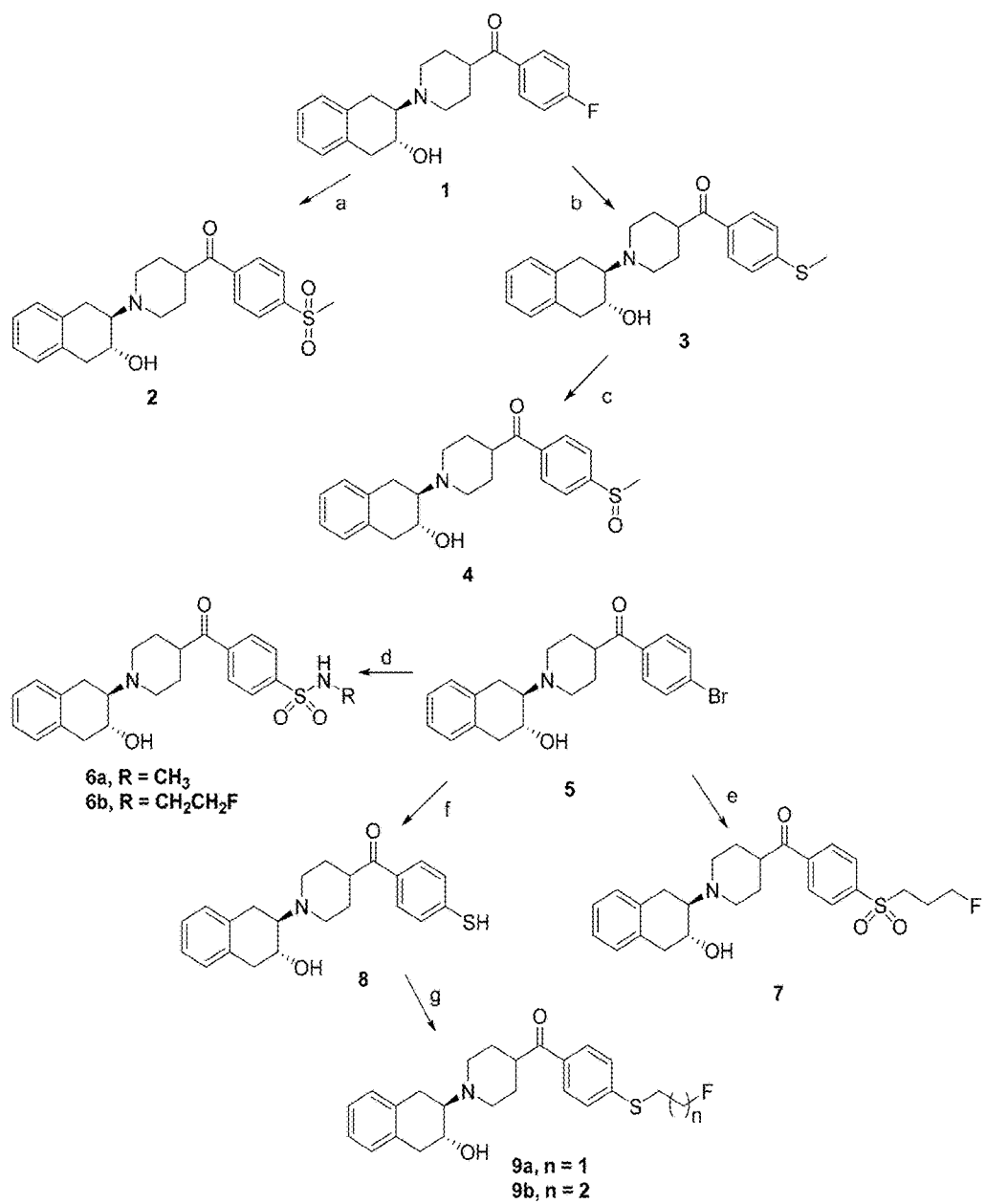
FIG. 2 shows the synthesis scheme for sulfur containing compounds (2), (3), and (4) from compound (1) and compounds (6a and 6b), (8), (7), and (9a and 9b) from compound (5). Reagents and conditions: (a) sodium methanesulfinate, DMSO, 100° C.; (b) sodium thiomethoxide, $K_2CO_3$, DMF, 55° C.; (c) $H_2O_2$, acetic acid, 55° C.; (d) (i) $K_2S_2O_5$, TBAB, sodium formate, $Pd(OAc)_2$, $PPh_3$, 1,10-phenanthroline, DMSO; (ii) NCS, methylamine hydrochloride or 2-fluoroethylamine hydrochloride, DIPEA, THF; (e) (i) $K_2S_2O_5$, TBAB, sodium formate, $Pd(OAc)_2$, $PPh_3$, 1,10-phenanthroline, DMSO; (ii) 1-bromo-3-fluoroprane, THF; (f) 1,2-ethanedithiol, Copper(II) sulfate pentahydrate, $Cs_2CO_3$, DMSO; (g) 1-bromo-2-fluoroethane or 1-bromo-3-fluoroprane, TBAB, $Cs_2CO_3$, DMF.

Starting from intermediate compounds (1) and (5), which were previously reported by the inventors, sulfur-containing compounds were routinely synthesized.[27] FIG. 2 shows the reaction scheme for producing Compounds (2), (3), and (4) from compound 1. Briefly, Compound (1) was reacted with sodium methanesulfinate to produce the sulfone (2) and sodium thiomethoxide to produce the sulfide (3), respectively. The sulfoxide (4) was easily prepared from the sulfide (3) by using $H_2O_2$ as oxidant in acetic acid.

FIG. 2 further shows a reaction scheme for producing Compounds (6a and 6b), (7), (8), and (9a and 9b) from the precursor compound (5). Briefly, palladium-catalyzed reaction of 5 in the presence of $K_2S_2O_5$ and sodium formate produced a sulfinate intermediate, which was used without isolation to afford the sulfonamides (6a and 6b) and the sulfone (7) by reacting with different commercially available amines and 1-bromo-3-fluoroprane, respectively.[28] Compounds 9a and 9b were prepared by reacting 1-bromo-2-fluoroethane or 1-bromo-3-fluoroprane with aryl thiol (8) in the presence of tetrabutylammonium bromide (TBAB) and $Cs_2CO_3$ in DMF, respectively. The aryl thiol (8) was obtained through a highly efficient copper-catalyzed single step synthesis from (5).[29] All the compounds were converted to their oxalate form before the binding assays (described in Example 12).

Example 2: Synthesis of (1-(3-Hydroxy-1,2,3,4-tetrahydronaphthalen-2-yl)piperidin-4-yl)(4 (methylsulfonyl)phenyl)methanone (2)

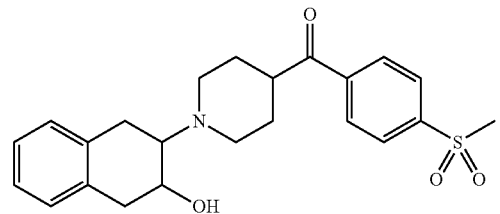

To a round-bottomed flask equipped with a magnetic stir bar was added 1 (0.35 g, 1.0 mmol), sodium methanesulfinate (0.11 g, 1.1 mmol), and DMSO (10 mL) under nitrogen. The reaction vessel was immersed in a 100° C. preheated oil bath for 24 h. After cooling, the mixture was diluted with water and extracted with ethyl acetate. The ethyl acetate layer was washed with saturated brine and dried over anhydrous Na$_2$SO$_4$. After filtering, the filtrate was concentrated under reduced pressure. The crude product was purified on a silica gel column, eluted with hexane/ethyl acetate (1/1, V/V) to afford 2 (0.15 g, 37%) as a gray solid. $^1$H NMR (400 MHz, CDCl$_3$) δ 8.18-8.02 (m, 4H), 7.17-7.08 (m, 4H), 4.17 (s, 1H), 3.95-3.80 (m, 1H), 3.34-3.28 (m, 2H), 3.09 (s, 3H), 3.02-3.00 (m, 1H), 2.92-2.77 (m, 6H), 2.45 (t, J=11.3 Hz, 1H), 1.98-1.90 (m, 3H), 1.87-1.80 (m, 1H). $^{13}$C NMR (101 MHz, CDCl$_3$) δ 200.84, 144.04, 140.09, 134.51, 133.88, 129.28, 129.08 (2C), 127.90, 126.21, 126.04, 66.51, 65.59, 51.69, 44.63, 44.30, 44.28, 37.76, 29.21, 28.89, 26.09. HRMS (ESI) Calculated for $C_{23}H_{27}NO_4S$ (M+H)$^+$ 414.1739, found: 414.1735. Enantiomers of (±)-2 was resolved by HPLC using a Chiralcel OD column (250 mm×10 mm), ethanol as mobile phase, flow rate of 4.0 mL/min, and UV wavelength at 254 nM to give (+)-2 and (−)-2, respectively. The free base of (+)-2 and (−)-2 were converted to oxalate salt as the general procedure. (+)-2 oxalate, Mp: 203-206° C., $[α]_D^{20}$=+43° (c=1, methanol); (−)-2 oxalate, Mp: 207-211° C., $[α]_D^{20}$=−43° (c=1, methanol).

Example 3: Synthesis of (1-(3-Hydroxy-1,2,3,4-tetrahydronaphthalen-2-yl)piperidin-4-yl)(4-(methylthio)phenyl)methanone (3)

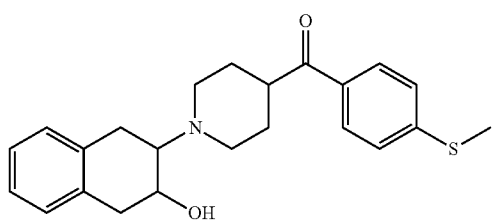

To a round-bottomed flask equipped with a magnetic stir bar was added 1 (0.18 g, 0.5 mmol), sodium thiomethoxide (0.07 g, 1.0 mmol), potassium carbonate (0.14 g, 1.0 mmol) and DMF (3 mL) under nitrogen. The reaction vessel was immersed in a 60° C. preheated oil bath for 9 h. The mixture was then cooled to room temperature and diluted with water, extracted with ethyl acetate. The organic layer was washed with saturated brine, dried over anhydrous $Na_2SO_4$, filtered, and concentrated under reduced pressure. The crude product was purified on a silica gel column, eluted with hexane/ethyl acetate (2/1, V/V) to afford 3 (0.11 g, 58%) as a yellow solid. $^1$H NMR (400 MHz, $CDCl_3$) δ 7.86 (d, J=8.5 Hz, 2H), 7.27 (d, J=8.5 Hz, 2H), 7.13-7.08 (m, 4H), 4.22 (s, 1H), 3.91-3.81 (m, 1H), 3.36-3.21 (m, 2H), 3.02-2.93 (m, 1H), 2.92-2.73 (m, 6H), 2.51 (s, 3H), 2.45-2.36 (m, 1H), 1.95-1.90 (m, 3H), 1.87-1.75 (m, 1H). $^{13}$C NMR (101 MHz, $CDCl_3$) δ 201.34, 145.84, 134.68, 133.95, 132.16, 129.26, 129.11, 128.66, 126.15, 126.00, 125.09, 66.53, 65.60, 51.91, 44.73, 43.54, 37.82, 29.57, 29.23, 26.09, 14.77. HRMS (ESI) Calculated for $C_{23}H_{27}NO_2S$ (M+H)$^+$ 382.1841, found: 382.1837. Enantiomers of (±)-3 was resolved by HPLC using a Chiralcel OD column (250 mm×10 mm), ethanol as mobile phase, flow rate of 4.0 mL/min, and UV wavelength at 254 nM to give (+)-3 and (−)-3, respectively. The free base of (+)-3 and (−)-3 were converted to oxalate salt as the general procedure. (+)-3 oxalate, Mp: 199-205° C., $[α]_D^{20}$=+66° (c=1, methanol); (−)-3 oxalate, Mp: 207-211° C., $[α]_D^{20}$=−62° (c=1, methanol).

Example 4: Synthesis of (1-(3-Hydroxy-1,2,3,4-tetrahydronaphthalen-2-yl)piperidin-4-yl)(4-(methylsulfinyl)phenyl)methano-ne (4)

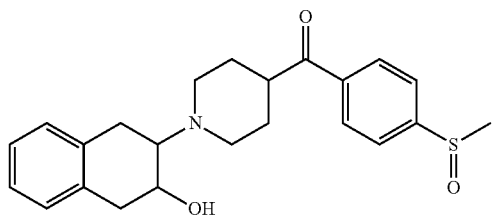

To a sealed tube equipped with a magnetic stir bar was added 3 (0.05 g, 0.13 mmol) and acetic acid (1.0 mL), after that, 30% $H_2O_2$ (13 μL, 0.13 mmol) was added into the mixture. The reaction vessel was immersed in a 55° C. preheated oil bath for 2 h. The mixture was then cooled to room temperature and basified with 1 M NaOH aqueous, extracted with ethyl acetate. The organic layer was washed with saturated brine, dried over anhydrous $Na_2SO_4$, filtered, and concentrated under reduced pressure. The crude product was purified on a silica gel column, eluted with dichloromethane/methanol (20/1, V/V) to afford 4 (0.03 g, 60%) as a yellow oil. $^1$H NMR (400 MHz, $CDCl_3$) δ 8.09 (d, J=8.5 Hz, 2H), 7.76 (d, J=8.5 Hz, 2H), 7.16-7.06 (m, 4H), 4.17 (s, 1H), 3.94-3.83 (m, 1H), 3.38-3.29 (m, 2H), 3.07-2.98 (m, 1H), 2.98-2.79 (m, 6H), 2.77 (s, 3H), 2.51-2.38 (m, 1H), 2.02-1.92 (m, 3H), 1.90-1.77 (m, 1H). $^{13}$C NMR (101 MHz, $CDCl_3$) δ 201.58, 151.00, 138.26, 134.68, 134.06, 129.41, 129.22 (2C), 126.35, 126.18, 124.01, 66.71, 65.78, 51.86, 44.87, 44.17, 43.96, 37.94, 29.47, 29.15, 26.27. HRMS (ESI) Calculated for $C_{23}H_{27}NO_3S$ (M+H)$^+$ 398.1790, found: 398.1786. The free base of 4 was converted to oxalate salt as the general procedure. 4 oxalate, Mp: 197-200° C.

Example 5: Synthesis of 4-(1-(3-Hydroxy-1,2,3,4-tetrahydronaphthalen-2-yl)piperidine-4-carbonyl)-N-methylbenzenesulfon-amide (6a)

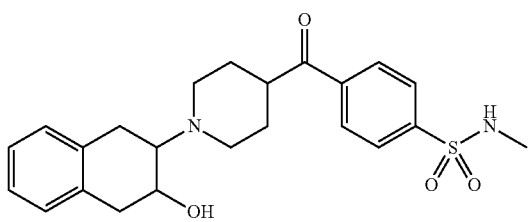

To a round-bottomed flask equipped with a magnetic stir bar was added potassium metabisulfite (54.7 mg, 0.25 mmol), tetrabutylammonium bromide (43.6 mg, 0.14 mmol), sodium formate (18.4 mg, 0.27 mmol), palladium acetate (2.8 mg, 0.01 mmol), triphenylphosphine (9.7 mg, 0.04 mmol), 1,10-phenanthroline (7.3 mg, 0.04 mmol) and DMSO (2.0 mL) under nitrogen. The mixture was bubbled with nitrogen for 10 min before 5 (50.8 mg, 0.12 mmol) was added. After that, the reaction vessel was immersed in a 70° C. preheated oil bath for 4 h. After cooling, diisopropylethylamine (23.8 mg, 0.19 mmol), methylamine hydrochloride (9.2 mg, 0.14 mmol) and THF (1.0 mL) were added into the above mixture. After cooling to 0° C., a solution of NCS (32.8 mg, 0.25 mmol) in THF (1.0 mL) was added, the reaction was stirred at room temperature overnight. The mixture was then diluted with water, extracted with ethyl acetate. The organic layer was washed with saturated brine, dried over anhydrous $Na_2SO_4$, filtered, and concentrated under reduced pressure. The crude product was purified on a silica gel column, eluted with dichloromethane/methanol (30/1, V/V) to afford 6a (35 mg, 66%) as a yellow oil. $^1$H NMR (400 MHz, $CD_3OD$) δ 8.07 (d, J=8.4 Hz, 2H), 7.97 (d, J=8.4 Hz, 2H), 7.17-7.07 (m, 4H), 4.46 (s, 1H), 3.93-3.83 (m, 1H), 3.38-3.26 (m, 2H), 3.06-2.98 (m, 1H), 2.95-2.79 (m, 6H), 2.72 (d, J=4.3 Hz, 3H), 2.49-2.38 (m, 1H), 2.04-1.90 (m, 3H), 1.89-1.77 (m, 2H). $^{13}$C NMR (101 MHz, $CDCl_3$) δ 201.24, 142.82, 139.24, 134.50, 133.89, 129.27, 129.06, 128.88, 127.58, 126.21, 126.03, 66.55, 65.62, 51.66, 44.68, 44.20, 37.77, 29.66, 29.32, 29.25, 28.94, 26.10. HRMS (ESI) Calculated for $C_{23}H_{28}N_2O_4S$ (M+H)$^+$ 429.1848, found: 429.1844. The free base of 6a was converted to oxalate salt as the general procedure. 6a oxalate, Mp: 200-205° C.

Example 6: Synthesis of N-(2-fluoroethyl)-4-(1-(3-hydroxy-1,2,3,4-tetrahydronaphthalen-2-yl)piperidine-4-carbonyl)benzenesulfonamide (6b)

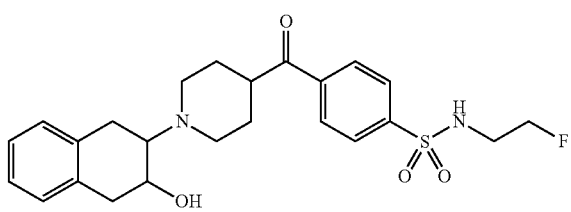

6b

To a round-bottomed flask equipped with a magnetic stir bar was added potassium metabisulfite (106.7 mg, 0.48 mmol), tetrabutylammonium bromide (85.1 mg, 0.26 mmol), sodium formate (35.9 mg, 0.53 mmol), palladium acetate (5.4 mg, 0.02 mmol), triphenylphosphine (18.9 mg, 0.07 mmol), 1,10-phenanthroline (14.3 mg, 0.07 mmol) and DMSO (2.0 mL) under nitrogen. The mixture was bubbled with nitrogen for 10 min before 5 (100 mg, 0.24 mmol) was added. After that, the reaction vessel was immersed in a 70° C. preheated oil bath for 4 h. After cooling, diisopropylethylamine (61.9 mg, 0.48 mmol), 2-fluoroethylamine hydrochloride (29.2 mg, 0.26 mmol) and THF (1.0 mL) were added into the above mixture. After cooling to 0° C., a solution of NCS (64.1 mg, 0.48 mmol) in THF (1.0 mL) was added, the reaction was stirred at room temperature overnight. The mixture was then diluted with water, extracted with ethyl acetate. The organic layer was washed with saturated brine, dried over anhydrous $Na_2SO_4$, filtered, and concentrated under reduced pressure. The crude product was purified on a silica gel column, eluted with dichloromethane/methanol (30/1, V/V) to afford 6b (20 mg, 10%) as a yellow oil. $^1$H NMR (400 MHz, $CDCl_3$) δ 8.07 (d, J=8.4 Hz, 2H), 7.98 (d, J=8.4 Hz, 2H), 7.18-7.06 (m, 4H), 4.93 (s, 1H), 4.54 (t, J=4.7 Hz, 1H), 4.42 (t, J=4.8 Hz, 1H), 3.94-3.83 (m, 1H), 3.75 (t, J=6.3 Hz, 1H), 3.41-3.34 (m, 1H), 3.34-3.28 (m, 2H), 3.07-2.99 (m, 1H), 2.95-2.77 (m, 6H), 2.50-2.40 (m, 1H), 2.02-1.91 (m, 3H), 1.88-1.81 (m, 2H). $^{13}$C NMR (101 MHz, cdcl$_3$) δ 201.33, 143.93, 139.54, 134.65, 134.09, 129.46, 129.24, 129.17, 127.56, 126.42, 126.23, 82.34 (d, $J_{C-F}$=169.7 Hz), 68.13, 66.75, 65.83, 51.78, 44.91, 43.70 (d, $J_{C-F}$=21.2 Hz), 37.97, 29.86, 26.32, 25.77. HRMS (ESI) Calculated for $C_{24}H_{29}FN_2O_4S$ (M+H)$^+$ 461.1910, found: 461.1907. The free base of 6b was converted to oxalate salt as the general procedure. 6b oxalate, Mp: 205-210° C.

Example 7: Synthesis of (4-((3-Fluoropropyl)sulfonyl)phenyl)(1-(3-hydroxy-1,2,3,4-tetrahydronaphthalen-2-yl)piperidin-4-yl)methanone (7)

7

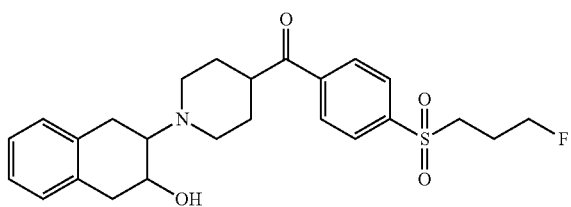

To a round-bottomed flask equipped with a magnetic stir bar was added potassium metabisulfite (88.9 mg, 0.40 mmol), tetrabutylammonium bromide (46.2 mg, 0.22 mmol), sodium formate (29.9 mg, 0.44 mmol), palladium acetate (2.2 mg, 0.01 mmol), triphenylphosphine (7.9 mg, 0.03 mmol), 1,10-phenanthroline (5.9 mg, 0.03 mmol) and DMSO (2.0 mL) under nitrogen. The mixture was bubbled with nitrogen for 10 min before 5 (80 mg, 0.2 mmol) was added. After that, the reaction vessel was immersed in a 70° C. preheated oil bath for 4 h. After cooling, 1-bromo-3-fluoropropane (20.9 mg, 0.15 mmol) in DMF (1.0 mL) were added into the above mixture, the reaction was stirred at room temperature overnight. The mixture was then diluted with water, extracted with ethyl acetate. The organic layer was washed with saturated brine, dried over anhydrous $Na_2SO_4$, filtered, and concentrated under reduced pressure. The crude product was purified on a silica gel column, eluted with hexane/ethyl acetate (½, V/V) to afford 7 (30 mg, 44%) as a gray solid. $^1$H NMR (400 MHz, $CDCl_3$) δ 8.04 (d, J=8.4 Hz, 2H), 7.97 (d, J=8.2 Hz, 2H), 7.09-7.00 (m, 4H), 4.52 (t, J=4.8 Hz, 1H), 4.40 (t, J=4.9 Hz, 1H), 3.88-3.77 (m, 1H), 3.34-3.15 (m, 4H), 3.01-2.91 (m, 1H), 2.90-2.69 (m, 6H), 2.38 (t, J=10.7 Hz, 1H), 2.18-2.02 (m, 2H), 1.96-1.83 (m, 3H), 1.81-1.70 (m, 1H). $^{13}$C NMR (101 MHz, $CDCl_3$) δ 201.30, 142.68, 140.44, 134.62, 134.05, 129.42, 129.21, 128.71, 126.38, 126.20, 125.91, 81.51 (d, $J_{C-F}$=168.7 Hz), 66.73, 65.80, 52.57 (d, $J_{C-F}$=4.0 Hz), 51.72, 44.87, 44.40, 37.94, 29.33, 29.02, 26.29, 24.09 (d, $J_{C-F}$=20.2 Hz). HRMS (ESI) Calculated for $C_{25}H_{30}FNO_4S$ (M+H)$^+$ 460.1958, found: 460.1954. The free base of 7 was converted to oxalate salt as the general procedure. 7 oxalate, Mp: 201-205° C.

Example 8: Synthesis of (1-(3-Hydroxy-1,2,3,4-tetrahydronaphthalen-2-yl)piperidin-4-yl)(4-mercaptophenyl)methanone (8)

8

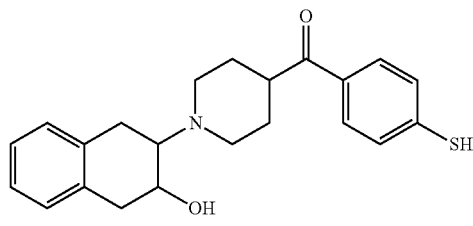

To a pressure tube containing a magnetic stir bar was added 5 (124.3 mg, 0.3 mmol), copper sulfate pentahydrate (3.7 mg, 0.015 mmol), $Cs_2CO_3$ (690.5 mg, 1.5 mmol) and DMSO (2.0 mL). The mixture was bubbled with nitrogen for 10 min before 1,2-ethanedithiol (56.5 mg, 0.6 mmol) was added. The tube was sealed and immersed in a 110° C. preheated oil bath for 12 h. The mixture was then cooled to room temperature and diluted with ethyl acetate, washed with water and saturated brine, dried over anhydrous $Na_2SO_4$, filtered, and concentrated under reduced pressure. The crude product was purified on a silica gel column, eluted with dichloromethane/methanol (20/1, V/V) to afford 8 (53 mg, 48%) as a yellow solid. $^1$H NMR (300 MHz, $CDCl_3$) δ 7.90 (d, J=8.5 Hz, 2H), 7.57 (d, J=8.4 Hz, 1H), 7.32 (d, J=8.4 Hz, 1H), 7.15-7.08 (m, 4H), 3.87 (s, 1H), 3.35-3.20 (m, 2H), 3.03-2.71 (m, 7H), 2.41 (s, 1H), 1.91-1.75 (m, 4H).

Example 9: Synthesis of (4-((2-Fluoroethyl)thio)phenyl)(1-(3-hydroxy-1,2,3,4-tetrahydronaphthalen-2-yl)piperidin-4-yl)methanone (9a)

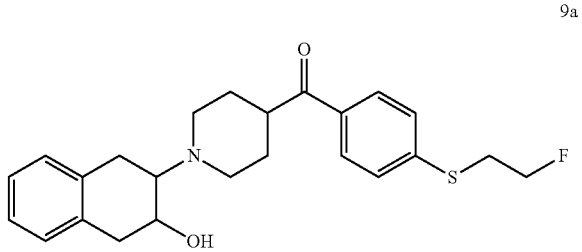 [SMILES: O=C(c1ccc(SCCF)cc1)C1CCN(C2Cc3ccccc3CC2O)CC1]

9a

To a round-bottomed flask equipped with a magnetic stir bar was added 8 (150 mg, 0.4 mmol), $Cs_2CO_3$ (133 mg, 0.4 mmol), TBAB (129 mg, 0.4 mmol) and DMF (2.0 mL) under nitrogen. After that, 1-bromo-2-fluoroethane (61 mg, 0.48 mmol) was added slowly via syringe. The reaction was stirred at room temperature for 7 h. The mixture was then cooled to room temperature and diluted with ethyl acetate, washed with water and saturated brine, dried over anhydrous $MgSO_4$, filtered, and concentrated under reduced pressure. The crude product was purified on a silica gel column, eluted with hexane/ethyl acetate (1/1, V/V) to afford 9a (65 mg, 39%) as a white solid. $^1$H NMR (400 MHz, $CDCl_3$) δ 7.87 (d, J=8.4 Hz, 2H), 7.39 (d, J=8.4 Hz, 2H), 7.17-7.07 (m, 4H), 4.66 (t, J=6.6 Hz, 1H), 4.55 (t, J=6.6 Hz, 1H), 3.92-3.83 (m, 1H), 3.36-3.23 (m, 4H), 3.04-2.76 (m, 8H), 2.42 (t, J=11.2 Hz, 1H), 1.99-1.90 (m, 3H), 1.89-1.75 (m, 1H). $^{13}$C NMR (101 MHz, $CDCl_3$) δ 201.33, 142.41, 134.62, 133.94, 133.36, 129.27, 129.09, 128.87, 127.39, 126.17, 126.01, 81.86 (d, $J_{C-F}$=173.7 Hz), 66.53, 65.61, 51.79, 44.74, 43.59, 37.79, 32.05 (d, $J_{C-F}$=22.2 Hz), 29.46, 29.13, 26.09. HRMS (ESI) Calculated for $C_{24}H_{28}FNO_2S$ (M+H)$^+$ 414.1903, found: 414.1899. Enantiomers of (±)-9a was resolved by HPLC using a Chiralcel OD column (250 mm×10 mm), ethanol as mobile phase, flow rate of 4.0 mL/min, and UV wavelength at 254 nM to give (+)-9a and (−)-9a, respectively. The free base of (+)-9a and (−)-9a were converted to oxalate salt as the general procedure. (+)-9a oxalate, Mp: 208-210° C., $[α]_D^{20}$=+57° (c=1, methanol); (−)-9a oxalate, Mp: 207-209° C., $[α]_D^{20}$=−52° (c=1, methanol).

Example 10: Synthesis of (4-((3-Fluoropropyl)thio)phenyl)(1-(3-hydroxy-1,2,3,4-tetrahydronaphthalen-2-yl)piperidin-4-yl)methanone (9b)

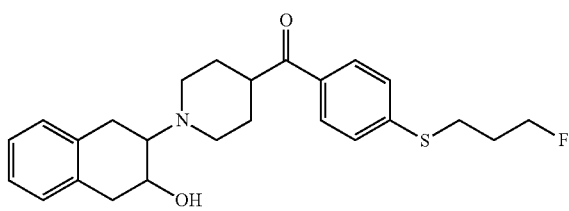

9b

To a round-bottomed flask equipped with a magnetic stir bar was added 8 (36.7 mg, 0.1 mmol), $Cs_2CO_3$ (32.5 mg, 0.1 mmol), TBAB (32.2 mg, 0.1 mmol) and DMF (1.5 mL) under nitrogen. After that, 1-bromo-3-fluoropropane (17 mg, 0.12 mmol) was added slowly via syringe. The reaction was stirred at room temperature for 3 h. The mixture was then cooled to room temperature and diluted with ethyl acetate, washed with water and saturated brine, dried over anhydrous $MgSO_4$, filtered, and concentrated under reduced pressure. The crude product was purified on a silica gel column, eluted with hexane/ethyl acetate (1/1, V/V) to afford 9b (26 mg, 61%) as a white solid. $^1$H NMR (300 MHz, $CDCl_3$) δ 7.87 (d, J=8.6 Hz, 2H), 7.34 (d, J=8.6 Hz, 2H), 7.16-7.07 (m, 4H), 4.66 (t, J=5.6 Hz, 1H), 4.51 (t, J=5.6 Hz, 1H), 3.92-3.83 (m, 1H), 3.35-3.28 (m, 2H), 3.14 (t, J=7.2 Hz, 2H), 3.02-2.96 (m, 1H), 2.93-2.76 (m, 6H), 2.46-2.37 (m, 1H), 2.20-1.99 (m, 2H), 1.99-1.79 (m, 4H). $^{13}$C NMR (101 MHz, $CDCl_3$) δ 201.37, 143.63, 134.63, 133.95, 132.84, 129.27, 129.09, 128.79, 126.73, 126.16, 126.00, 82.83 (d, $J_{C-F}$=167.7 Hz), 66.52, 65.60, 51.86, 44.73, 43.57, 37.78, 29.88, (d, $J_{C-F}$=20.2 Hz), 29.50, 29.16, 27.78 (d, $J_{C-F}$=5.1 Hz), 26.08. HRMS (ESI) Calculated for $C_{25}H_{30}FNO_2S$ (M+H)$^+$ 428.2060, found: 428.2056. Enantiomers of (±)-9a was separated by HPLC using a Chiralcel OD column (250 mm×10 mm), ethanol as mobile phase, flow rate of 4.0 mL/min, and UV wavelength at 254 nM to give (+)-9b and (−)-9b, respectively. The free base of (+)-9b and (−)-9b were converted to oxalate salt as the general procedure. (+)-9b oxalate, Mp: 214-217° C., $[α]_D^{20}$=+47° (c=1, methanol); (−)-9b oxalate, Mp: 207-209° C., $[α]_D^{20}$=−49° (c=1, methanol).

Example 11: Synthesis of (−)-Sodium 4-(1-(3-hydroxy-1,2,3,4-tetrahydronaphthalen-2-yl)piperidine-4-carbonyl)benzenesulfinate (10)

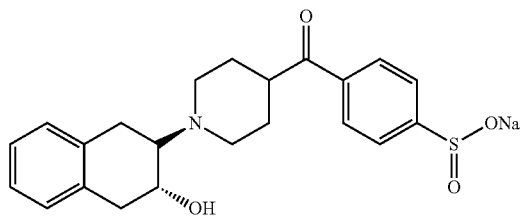

(−)-10

To a round-bottomed flask equipped with a magnetic stir bar was added potassium metabisulfite (88.9 mg, 0.40 mmol), tetraethylammonium bromide (46.2 mg, 0.22 mmol), sodium formate (29.9 mg, 0.44 mmol), palladium acetate (2.2 mg, 0.01 mmol), triphenylphosphine (7.9 mg, 0.03 mmol), 1,10-phenanthroline (5.9 mg, 0.03 mmol) and DMSO (2.0 mL). The mixture was bubbled with nitrogen for 10 min before (−)-5 (80 mg, 0.2 mmol) was added. After that, the reaction vessel was immersed in a 70° C. preheated oil bath for 4 h. After cooling, methanol was added and the mixture was filtered through celite. The filtrate was concentrated and the resulting oil was triturated with diethyl ether 2×20 mL. The resulting solid was filtered and dried under vacuum to afford the crude sulfonate, then purified by reverse HPLC on C18 column to get pure (−)-10.

Example 12: In Vitro Binding Affinity Studies

In vitro binding studies were performed to measure the affinities to the VAChT and $σ_1$ and $σ_2$ receptors. VAChT binding was assayed using membrane homogenate from PC12 cells which overexpress human VAChT.[8] The $\sigma_1$ and $\sigma_2$ binding affinities were assayed in rat brain and in guinea pig membranes, respectively. All the compounds were tested as their oxalate form, data is shown in Tables 1 and 2.

VAChT Binding:

The binding affinity of a compound to VAChT was measured by competition against the binding of 5 nM [$^3$H]Vesamicol to postnuclear supernatant prepared from PC12 cells stably expressing human VAChT according to the methods as previously described[32]. Nonspecific binding was determined from samples containing 1 µM of nonradioactive (±)-Vesamicol. The test compounds were assayed in increments of 10-fold from 0.1 to 10,000 nM concentration. The surfaces of containers were pre-coated with Sigmacote (Sigma-Aldrich, Mo.). Samples containing 200 µg postnuclear supernatant in 200 µL of 110 mM potassium tartrate, 20 mM HEPES (pH 7.4 with KOH), 1 mM dithiothreitol, and 0.02% sodium azide were incubated at 22° C. for 24 h. A volume of 90 µL was filtered in duplicate through GF/F glass fiber filters coated with polyethylenimine and washed. Filter-bound radioactivity was determined by liquid scintillation spectrometry for 10 min per sample. Averaged data were fitted by regression with a rectangular hyperbola to estimate $K_i$ value. All the compounds were independently assayed at least two times.

Sigma Receptor Binding:

The σ receptors binding affinity studies were performed following a previously reported procedure.[33,34] The compounds were dissolved in DMSO, and then diluted with 50 mM Tris-HCl buffer containing 150 mM NaCl and 100 mM EDTA at pH 7.4 before performing the $\sigma_1$ and $\sigma_2$ receptor binding measurement. Briefly, to measure the $\sigma_1$ receptor binding affinity, we use guinea pig brain membrane homogenates (~300 µg protein) tissues as the receptor resource and ~5 nM [$^3$H](+)-Pentazocine (34.9 Ci/mmol, Perkin Elmer, Boston, Mass.) as the radioligand. The mixture was incubated in 96-well plates for 90 min at room temperature. Nonspecific binding was determined from samples containing 10 µM of nonradioactive Haloperidol. After 90 min, the mixture was transferred into a 96-well fiberglass filter plate (Millipore, Billerica, Mass.) presoaked with 100 µL of 50 mM Tris-HCl buffer at pH 8.0 for 60 min, followed by addition of 150 µL of ice-cold wash buffer (10 mM Tris-HCl, 150 mM NaCl, pH 7.4). The harvested samples were filtered rapidly and washed with 3×200 µL portions of ice-cold wash buffer, and the filterers were counted by a Wallac 1450 MicroBeta liquid scintillation counter (Perkin-Elmer, Boston, Mass.). The $\sigma_2$ receptor binding affinity was determined using rat liver membrane homogenates (~300 µg protein) as the receptor resource and ~5 nM [$^3$H]DTG (58.1 Ci/mmol, Perkin-Elmer, Boston, Mass.) as the radioligand in the presence of 1 µM of (+)-Pentazocine which was used to block $\sigma_1$ sites. The mixture was incubated for 120 min at room temperature. Nonspecific binding was determined from samples containing 10 µM of nonradioactive Haloperidol. All other procedures were similar to those described for the $\sigma_1$ receptor binding assay above. Data from the competitive binding experiments were modeled using nonlinear regression analysis to determine the concentration that inhibits 50% of the specific binding of the radioligand. Competitive binding curves were best fit to a one-site fit and gave pseudo-Hill coefficients of 0.6-1.0. $K_i$ values were calculated using the method of Cheng and Prusoff,[35] then presented as the mean±SEM. Calculations were performed using a $K_d$ value of 7.89 nM for (+)-[$^3$H]Pentazocine in guinea pig brains and a $K_d$ value of 30.7 nM for [$^3$H]Ditolylguanidine in rat livers.

As shown in Table 1, all the ligands show good binding affinities to VAChT, especially compounds 2 (5.4 nM), 3 (2.4 nM), 9a (2.4 nM), and 9b (2.3 nM). The thioether 3 (2.4 nM) shows the better binding affinity than the sulfone 2 (5.4 nM) and the sulfoxide 4 (6.5 nM). The sulfamide ligands (6a, 6.3 nM; 6b, 13.0 nM) also show potent binding activities. These results suggest that the different sulfur-containing function group played a great impact on the binding affinities, and the thioether can give the best binding affinity

TABLE 1

Binding Affinities ($K_i$) of Sulfur-containing Compounds for VAChT[a]

| Compound[b] | Structure | $K_i$ (nM)[c] |
|---|---|---|
| 2 | 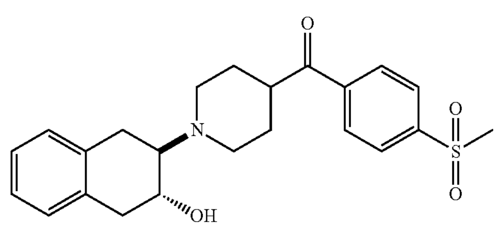 [SMILES: CS(=O)(=O)c1ccc(C(=O)C2CCN([C@@H]3Cc4ccccc4C[C@H]3O)CC2)cc1] | 5.4 ± 0.6 |
| 3 | 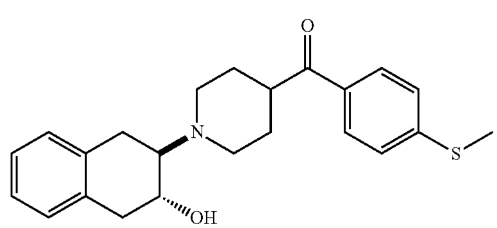 [SMILES: CSc1ccc(C(=O)C2CCN([C@@H]3Cc4ccccc4C[C@H]3O)CC2)cc1] | 2.4 ± 0.3 |

TABLE 1-continued

Binding Affinities ($K_i$) of Sulfur-containing Compounds for VAChT[a]

| Compound[b] | Structure | $K_i$ (nM)[c] |
| --- | --- | --- |
| 4 | 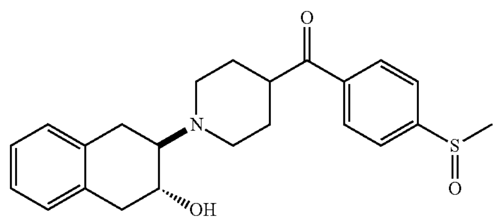 [SMILES: CS(=O)c1ccc(C(=O)C2CCN([C@@H]3Cc4ccccc4C[C@H]3O)CC2)cc1] | 6.5 ± 0.9 |
| 6a | 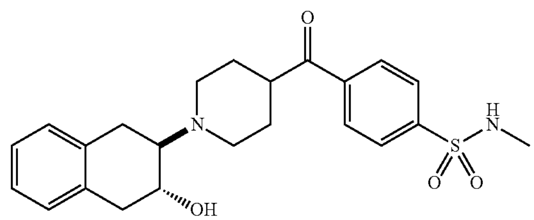 [SMILES: CNS(=O)(=O)c1ccc(C(=O)C2CCN([C@@H]3Cc4ccccc4C[C@H]3O)CC2)cc1] | 6.3 ± 0.8 |
| 6b | 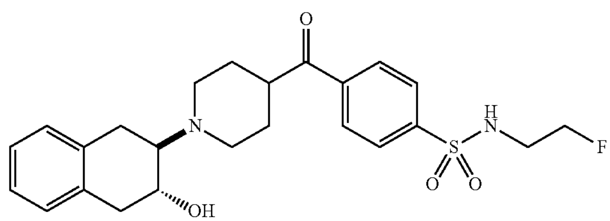 [SMILES: O=C(c1ccc(S(=O)(=O)NCCF)cc1)C1CCN([C@@H]2Cc3ccccc3C[C@H]2O)CC1] | 13.0 ± 1.0 |
| 7 | 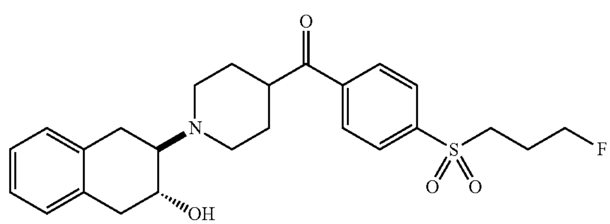 [SMILES: O=C(c1ccc(S(=O)(=O)CCCF)cc1)C1CCN([C@@H]2Cc3ccccc3C[C@H]2O)CC1] | 12.8 ± 0.7 |
| 9a | 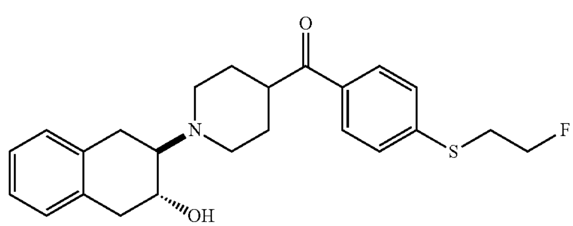 [SMILES: O=C(c1ccc(SCCF)cc1)C1CCN([C@@H]2Cc3ccccc3C[C@H]2O)CC1] | 2.4 ± 0.5 |
| 9b | 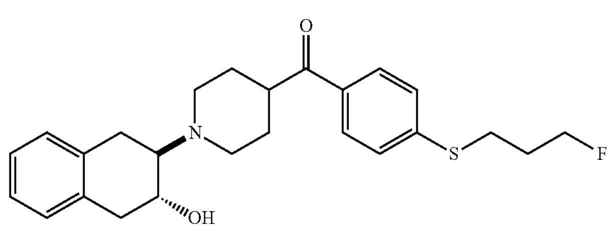 [SMILES: O=C(c1ccc(SCCCF)cc1)C1CCN([C@@H]2Cc3ccccc3C[C@H]2O)CC1] | 2.3 ± 0.4 |
| Vesamicol | | 9.9 ± 1.0 |

[a]$K_i$ values (mean ± SEM) were determined by at least three experiments.
[b]All the compounds were tested as their oxalate form.
[c]Expressed human VAChT was used for VAChT binding assay.
[d]Calculated value at pH 7.4 by ACD/Labs, version 7.0 (Advanced Chemistry Development, Inc., Canada).

Chirality can influence binding affinity for many ligands[8], including structurally similar compounds[27]. Since in vitro binding studies indicated that the racemic compounds 2, 3, 9a, and 9b displayed a high affinity to VAChT, these four compounds were further resolved from racemic mixture via chiral HPLC using chiral OD column to give (+)-2, (−)-2, (+)-3, (−)-3, (+)-9a, (−)-9a, (+)-9b, and (−)9b. The precursor (−)-8 and (−)-10 was synthesized from (−)-5 as described in Examples 8 and 11 which was separated on a chiral OD column. Each isomer was collected and converted to their oxalates for the VAChT binding assay. These compounds' binding selectivity to $\sigma_1$ and $\sigma_2$ receptor was determined in parallel. As shown in Table 2, all the minus isomers exhibit better binding affinities to VAChT than plus isomers. However, all the new ligands have moderate binding affinities to $\sigma_1$ receptor and poor binding affinities to $\sigma_2$ receptor.

TABLE 2

Binding Affinities ($K_i$) of Sulfur-containing Compounds for $\sigma_1$ Receptor, $\sigma_2$ Receptor, and VAChT[a]

| | | $K_i$ (nM) | | Selectivity ratio | |
| --- | --- | --- | --- | --- | --- |
| Compounds[b] | VAChT[c] | $\sigma_1$[d] | $\sigma_2$[e] | VAChT/$\sigma_1$ | VAChT/$\sigma_2$ |
| 2 | 5.4 ± 0.6 | 16.5 ± 2.1 | >1,000 | 3.1 | >185 |
| (+)-2 | 193 ± 17.8 | 18.5 ± 3.4 | >1,000 | 0.1 | >5 |
| (−)-2 | 4.1 ± 0.9 | 34.7 ± 4.9 | >1,000 | 8.5 | >243 |
| 3 | 2.4 ± 0.3 | 17.2 ± 4.0 | >1,000 | 7.2 | >416 |
| (+)-3 | 13.8 ± 1.1 | 23.3 ± 2.9 | >1,000 | 1.7 | >72 |
| (−)-3 | 1.4 ± 0.3 | 19.0 ± 5.6 | >1,000 | 13.6 | >714 |
| 9a | 2.4 ± 0.5 | 16.7 ± 2.1 | >1,000 | 7.0 | >416 |
| (+)-9a | 11.8 ± 2.7 | 14.4 ± 2.0 | >1,000 | 1.2 | >84 |
| (−)-9a | 2.2 ± 0.4 | 30.8 ± 4.1 | >1,000 | 13.4 | >454 |
| 9b | 2.3 ± 0.4 | 40.8 ± 4.1 | >1,000 | 17.7 | >434 |
| (+)-9b | 19.9 ± 9.2 | 38.6 ± 7.1 | >1,000 | 1.9 | >50 |
| (−)-9b | 1.4 ± 0.2 | 4.1 ± 0.7 | >1,000 | 2.9 | >714 |

[a]$K_i$ values (mean ± SEM) were determined by at least three experiments.
[b]All the compounds were tested as their oxalate form.
[c]Expressed human VAChT was used for VAChT binding assay.
[d]Homogenates of guinea pig brain was used for binding assay.
[e]Homogenates of rat liver was used for binding assay.

Given their high affinities for VAChT and to further understand the pharmacokinetic properties of these sulfur-containing ligands, (−)-3 and (−)-9a were radiolabeled with $^{11}$C and $^{18}$F, respectively and chosen for further validatation in rodents and nonhuman primates because of their high VAChT binding affinities (1.4 nM and 2.2 nM) and moderate selectivity to a receptor (13.6-fold and 13.4-fold).

Example 13: Radiochemistry and Generation of Radiolabeled Compounds

Figure 3:
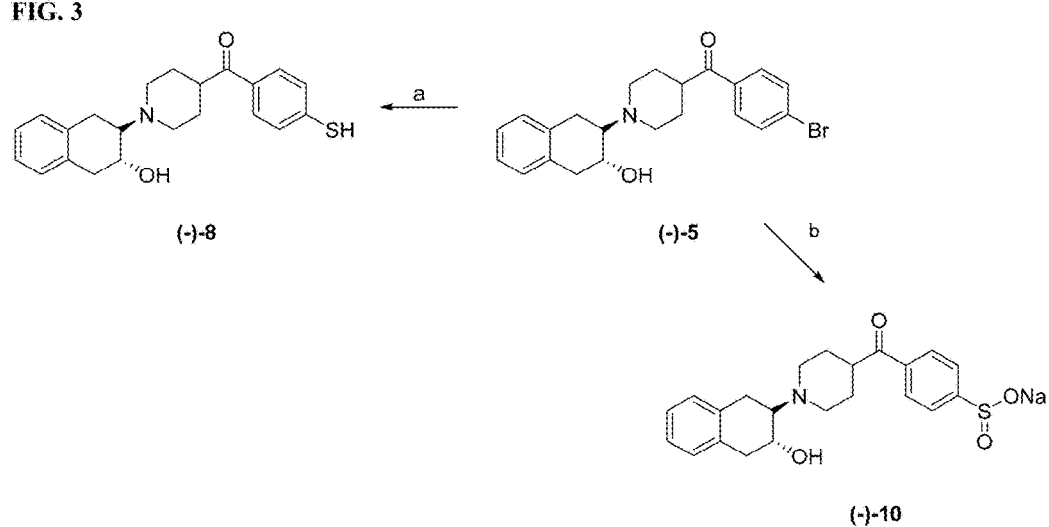
FIG. 3 shows the synthesis scheme for (−)-8 and (−)-10 from (−)-5. Reagents and conditions: (a) 1,2-ethanedithiol, Copper(II) sulfate pentahydrate, $Cs_2CO_3$, DMSO; (b) $K_2S_2O_5$, TBAB, sodium formate, $Pd(OAc)_2$, $PPh_3$, 1,10-phenanthroline, DMSO.

To further understand the pharmacokinetic property of these sulfur-containing ligands, (−)-2 and (−)-3 were radiolabeled with $^{11}$C and (−)-9a with $^{18}$F. Radiolabeled compounds were synthesized from precursors (−)-8, (−)-10 which in turn were derived from precursor (−)-5 as depicted in FIG. 3. Synthesis of racemic 8 is described in Example 8 and synthesis of (−)-10 was described in Example 11. Racemic mixtures were resolved via chiral HPLC on a chiral OD column. The reagents and conditions used to generate (−)-8 were: 1,2-ethanedithiol, Copper(II) sulfate pentahydrate, $Cs_2CO_3$, DMSO and those used to generate (−)-10 were: $K_2S_2O_5$, TBAB, sodium formate, $Pd(OAc)_2$, $PPh_3$, 1,10-phenanthroline, DMSO. Briefly, The radiosynthesis of (−)-[$^{11}$C]2 was successfully accomplished from precursor (−)-10 under $^{11}$CH$_3$I in DMF. (−)-[$^{11}$C]3 and (−)-[$^{18}$F]9a were synthesized from precursor (−)-8 under $^{11}$CH$_3$I and 2-(fluoro-$^{18}$F)ethyl 4-methylbenzenesulfonate in DMSO respectively with $Cs_2CO_3$ as base. These three new PET radiotracers were subjected to autoradiography evaluations on Sprague-Dawley rats and micro PET imaging studies on nonhuman primates.

Synthesis Overview for Radiolabeled (−)-2, (−)-3, and (−)-9a from Precursors (−)-8 and (−)-10.

Figure 4:
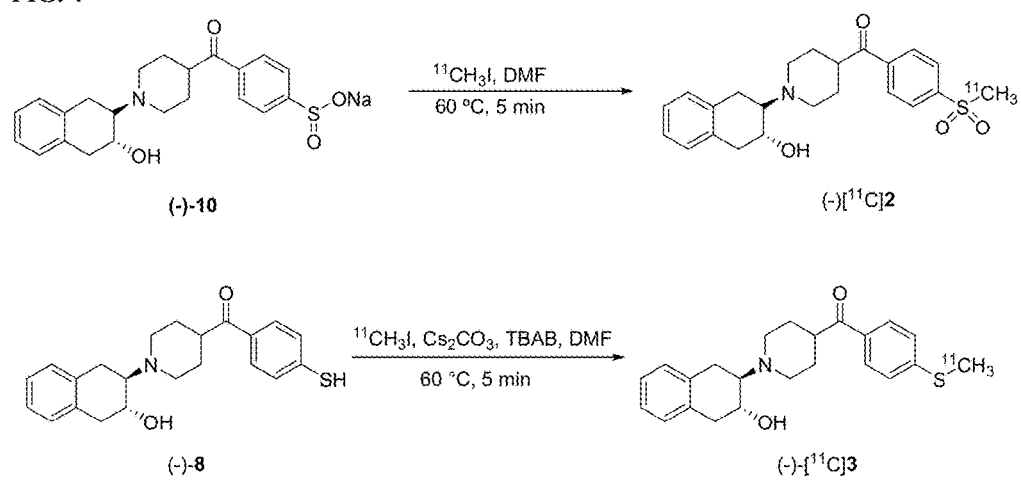
FIG. 4 shows the synthesis scheme for (−)-[$^{11}$C]2, (−)-[$^{11}$C]3 from (−)-10 and (−)-8, respectively. The reagents and conditions are depicted in the figure.
Figure 5:
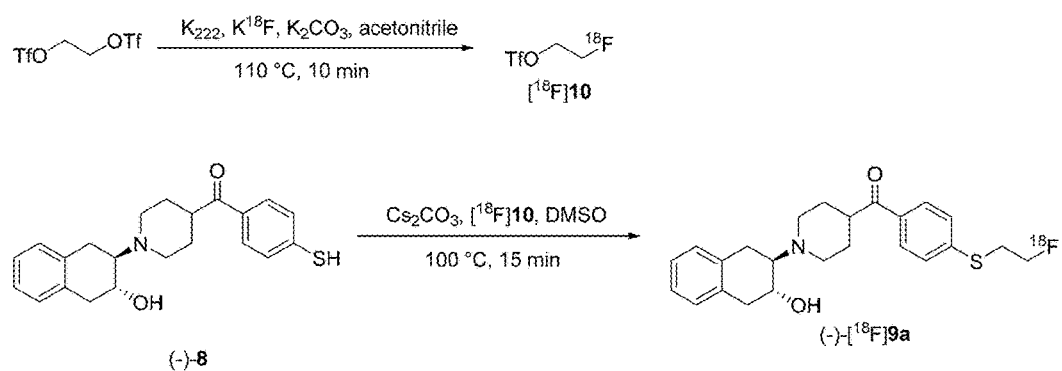
FIG. 5 shows the two step synthesis scheme for (−)-[$^{18}$F]9a from (−)-10. The reagents and conditions are depicted in the figure.

FIG. 4 depicts the reaction schemes for producing radiolabeled (−)-[$^{11}$C]2 and (−)-[$^{11}$C]3. The radiosynthesis of (−)-[$^{11}$C]2 was successfully accomplished from precursor (−)-10 under $^{11}$CH$_3$I in DMF. The radiosynthesis of (−)-[$^{11}$C]3 was synthesized by treating precursor (−)-8 with [$^{11}$C]CH$_3$I in the presence of $Cs_2CO_3$ and TBAB in DMF with a radiochemical yield of 50-60% (decay corrected to EOS, n=3). The radiosynthesis of (−)-[$^{18}$F]9a was accomplished by a two-step strategy as shown in FIG. 5.[30] First, ethylene ditosylate was reacted with [$^{18}$F]KF/Kryptofix 222 in acetonitrile and then purified on a reverse phase HPLC to afford [$^{18}$F]fluoroethyl tosylate ([$^{18}$F]10). Next, the precursor (−)-5 was reacted with [$^{18}$F]10 in DMSO in the presence of $Cs_2CO_3$ followed by purification on HPLC afforded (−)-[$^{18}$F]9a with a 60-70% radiochemical yield (decay corrected to end of synthesis, n=5). The radioactive (−)-[$^{11}$C]3 or (−)-[$^{18}$F]9a were authenticated by co-injecting with the standard reference (−)-3 or (−)-9a on an analytical HPLC system, respectively.

Detailed Synthesis Procedures for Radiolabeled (−)-3 and (−)-9a.

Radiosynthesis of (−)-[$^{11}$C]3.

Approximately 1~2 mg of the precursor (−)-8 was placed in a reaction vessel with a saturated solution of $Cs_2CO_3$ and TBAB in DMF (0.2 mL). [$^{11}$C]CH$_3$I was bubbled into the reaction vessel and the reaction mixture was heated at 60° C. for 5 min. After quenching with 1.8 mL of HPLC mobile phase (40% acetonitrile in 0.1 M ammonium formate buffer, pH 4.5), The mixture was loaded on to a C-18 column (Phenomenex Luna C18, 250 mm×9.6 mm) with a UV detector set at 254 nm, then separated by using the above HPLC mobile phase at a flow rate of 4.0 mL/min. The radioactive product was collected between 13 and 15 min into 50 mL sterile water. The aqueous solution was passed through C18 Sep-Pak Plus by applying air pressure. The vial was rinsed with 20 mL of sterile water which was also passed through the Sep-Pak Plus. The trapped product was eluted with 0.6 mL of ethanol and 5.4 mL of saline to formulate the injection dose. The product was authenticated using an analytical HPLC system by co-injecting with standard reference compound (−)-3. The radiochemical yield was 50-60% (decay corrected to end of synthesis, n=3) with the radiochemical purity of >99% and the specific activity was >74 GBq/μmol (EOS).

Radiosynthesis of 1-[$^{18}$F]Fluoro-2-Tosyloxyethane ([$^{18}$F]10).

A solution of ~7.0 GBq [$^{18}$F]/fluoride was added to a reaction vessel containing Kryptofix 222 (6.0-7.0 mg). Acetonitrile (3×1.0 mL) was added to the mixture to remove water using nitrogen gas to bubble the mixture at ~110° C. After removing the water, 1, 2-ethylene ditosylate (5.0-6.0 mg) was dissolved into acetonitrile (0.2 mL) under vortex, and then the solution was transferred to the reaction vessel containing [$^{18}$F]fluoride/Kryptofix 222/$K_2CO_3$. The reaction vessel was capped and the reaction mixture was immersed into a 110° C. preheated oil bath for 10 min. Subsequently, the oil bath was removed and the reaction mixture was quenched using 2.8 mL of HPLC mobile phase (50% acetonitrile in 0.1 M ammonium formate, pH 6.5) followed by passing through an alumina Neutral Sep-Pak Plus cartridge. The crude product was then loaded onto a C-18 column (Agilent SB-C18, 250 mm×10 mm) with a UV detector set at 254 nm, then separated by using the above HPLC mobile phase at a flow rate of 4.0 mL/min. The radioactive product was collected between 9 min and 10 min in 50 mL sterile water, then passed through a C-18 Sep-Pak Plus cartridge to trap [$^{18}$F]10 on the Sep-Pak. Ether (3.0 mL) was used to elute the radioactivity to afford [$^{18}$F]10 (1.3-1.9 MBq, 30-50% radiochemical yield, decay corrected to EOS).

Radiosynthesis of (−)-[$^{18}$F]9a.

The upper ether layer of the eluted solution of [$^{18}$F]10 was transferred into a vial, and the lower aqueous phase was extracted with another 1 mL of ether. The combined ether solution was passed through a set of two Sep-Pak Plus Na$_2$SO$_4$ dry cartridges into a reaction vessel. After the ether was evaporated with a nitrogen stream at room temperature, the solution of precursor (−)-8 (1.0-2.0 mg) in DMSO (200 µL) and Cs$_2$CO$_3$ (1.0-2.0 mg) were added to the reaction vessel containing [$^{18}$F]10. The vessel was capped and heated at 100° C. for 15 min. Subsequently, the reaction mixture was diluted with 3.0 mL HPLC mobile phase (40% acetonitrile in 0.1 M ammonium formate buffer, pH 4.5) and loaded onto a C-18 column (Agilent SB-C18, 250 mm×10 mm) with a UV detector set at 254 nm, then separated by using the above HPLC mobile phase at a flow rate of 4.0 mL/min. The radioactive product was collected between 20 min and 23 min into 50 mL sterile water, then passed through a C-18 Sep-Pak Plus cartridge to trap (−)-[$^{18}$F]9a on the Sep-Pak. The trapped product was eluted with 0.6 mL of ethanol and 5.4 mL of saline to formulate the injection dose. The product was authenticated using an analytical HPLC system by co-injecting with standard reference compound (−)-9a. The radiochemical yield was 60-70% (decay corrected to EOS, n=5) with the radiochemical purity of >95% and the specific activity was >55 GBq/µmol (decay corrected to EOS).

Example 14: Ex Vivo Autoradiography Studies

Figure 6:
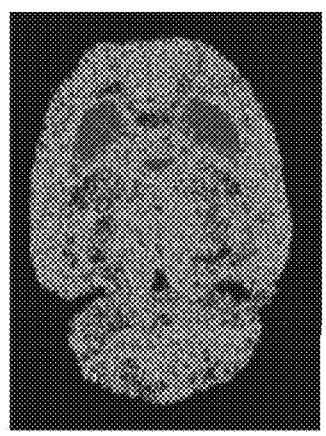
FIG. 6 shows autoradiography images of (−)-[$^{11}$C]3 and (−)-[$^{18}$F]9a in the male Sprague-Dawley (SD) rat brain (A and C). Quantification is shown in (B and D). The representative horizontal slice (100 μm thick) of the SD rat brain shows the highest accumulation of radioactivity in the VAChT enriched striatal regions (B and D). Quantification of autoradiography are from entire 30 brain slices at 60 min post-injection. Histograms are the average of photostimulated luminescence per square millimeter of 30 brain slices. Error bars are the standard derivations.
Figure 6:
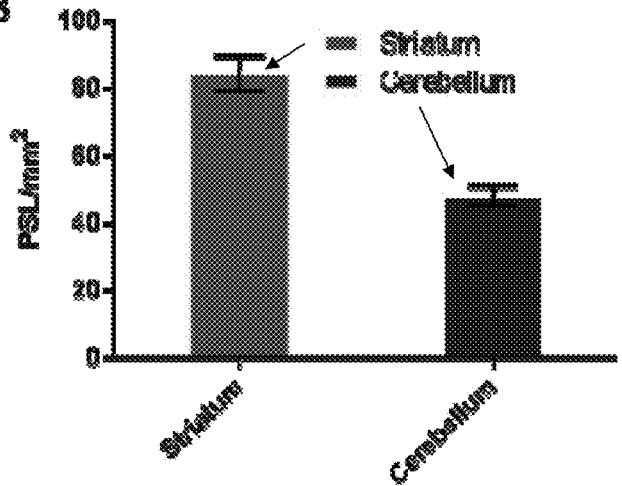
Figure 6:
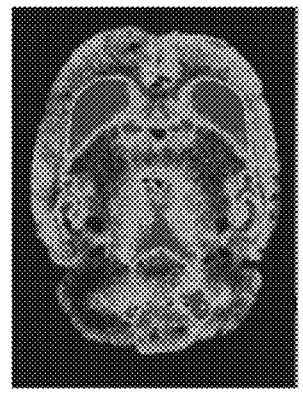
Figure 6:
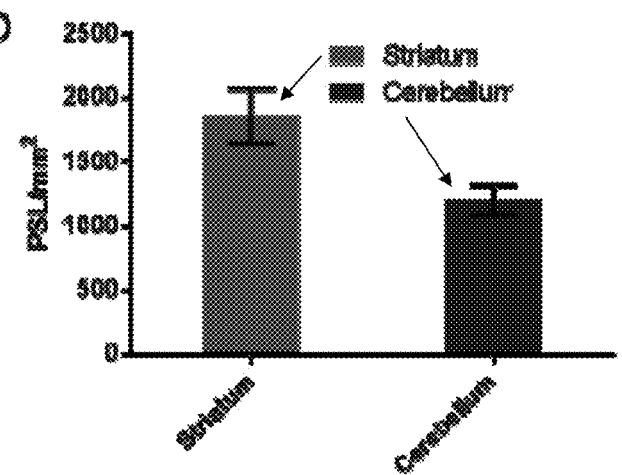

Ex vivo autoradiography was performed on 6-8 month old male Sprague-Dawley rats to confirm the brain distribution of radiolabeled VAChT ligands. Mature male Sprague-Dawley rats were injected with ~500 µCi of (−)-[$^{11}$C]3 or (−)-[$^{18}$F]9a via the tail vein under isoflurane/oxygen anesthesia, respectively. The rats were euthanized after 1 h and the brains were quickly removed and placed in a metal brain matrix with slots spaced at 1 mm intervals. The brains were then frozen in the matrix and sectioned into 100 µm coronal slices. Brain slices were carefully removed from the brain matrix razor blades and placed on a clear sheet covered with film and mounting on glass slides. Then, the brain sections were exposed to the film in an imaging cassette for 12 h before they were counted by the FLA7000. Photographic images were obtained using a flatbed scanner. The autoradiograms (FIGS. 6A and 6C) indicated that both (−)-[$^{11}$C]3 and (−)-[$^{18}$F]9a have a high accumulation in the VAChT enriched striatum. There was also moderate uptake in other regions, which may be caused by the moderate binding activity to σ$_1$ receptor. The quantification of autoradiography from entire 30 brain slices indicated the uptake ratio of radioactivity in striatum versus cerebellum reached 1.75 and 1.54, respectively. (FIGS. 6B and 6D)

Example 15: MicroPET Imaging Studies in Non-Human Primates (NHPs)

The promising results from ex vivo autoradiography in rats suggested that (−)-[$^{11}$C]3 and (−)-[$^{18}$F]9a have potential to be a suitable tracer for studying cholinergic innervations via VAChT in humans. Therefore, the MicroPET imaging in the brains of male cynomolgus monkeys was performed to determine their potential as a PET tracer for imaging the VAChT in vivo.

PET studies were performed on adult male cynomolgus monkeys (6-8 kg) with a MicroPET Focus 220 scanner (Concorde/CTI/Siemens Microsystems, Knoxville, Tenn.). The animal was anesthetized using an intramuscular injection with ketamine (10-20 mg/kg) and glycopyrrolate (0.013-0.017 mg/kg) and then transported to the PET scanner suit. After arrival, the animal was intubated with an endotracheal tube and anesthesia was maintained at 0.75-2.0% isoflurane/oxygen throughout the procedure, and then a percutaneous venous catheter was placed for radiotracer injection. A heated water blanket was used to keep the temperature at 37° C. In each MicroPET scanning session, the head was positioned supine in the adjustable head holder with the brain in the center of the field of view. A 10-min transmission scan was performed to check positioning; once confirmed, a 45 min transmission scan was obtained for attenuation correction. Subsequently, a 2 h dynamic emission scan was acquired after administration of 296-410 MBq of (−)-[$^{11}$C]3 or (−)-[$^{18}$F]9a via the venous catheter. PET scans were collected from 0-120 min with the following time frames: 3×1 min, 4×2 min, 3×3 min and 20×5 min. PET image reconstructed resolution was <2.0 mm full width half maximum for all 3 dimensions at the center of the field of view. Emission data were corrected using individual attenuation and model-based scatter correction and reconstructed using filtered back projection. The first baseline PET image for each animal acted as the target image with the MPRAGE and subsequent PETs co-registered using automated image registration program AIR. All MPRAGE-based volume of interest (VOI) analyses were accomplished by experienced investigators. For quantitative analyses, three-dimensional ROIs (striatum, cerebellum, frontal cortex, occipital cortex, temporal, midbrain, hippocampus and thalamus) were transformed to the baseline PET space and then overlaid on all reconstructed PET images to obtain time-activity curves. Activity measures were standardized to body weight and dose of radioactivity injected to yield standardized uptake value (SUV).

Figure 7:
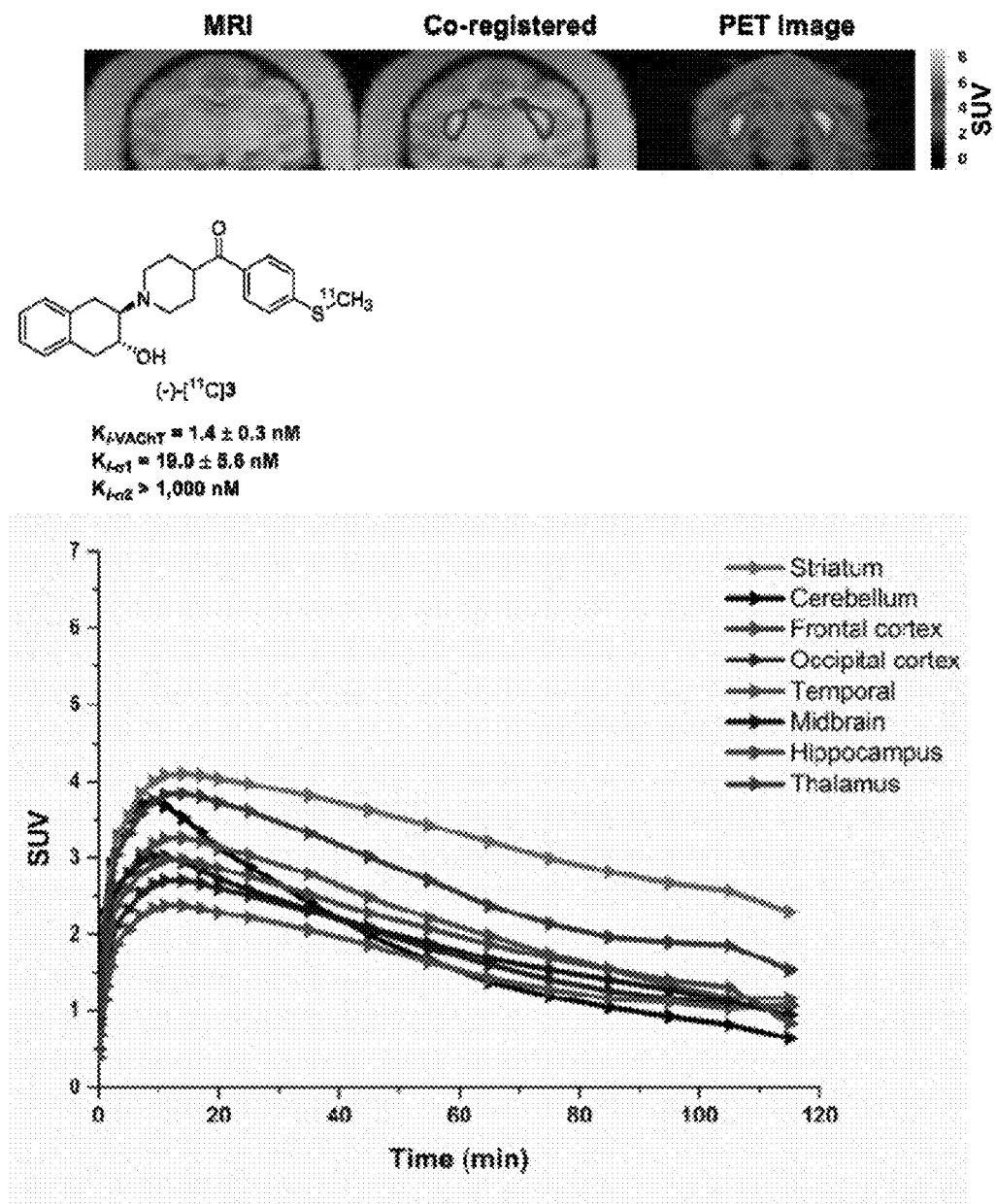
FIG. 7 is MicroPET imaging studies of (−)-[11C]3 on cynomolgus monkeys: MRI image (top left), co-registered image (top middle), and MicroPET image (top right); Tissue time-activity curves of (−)-[11C]3 in cynomolgus monkey brain (bottom left).
Figure 8:
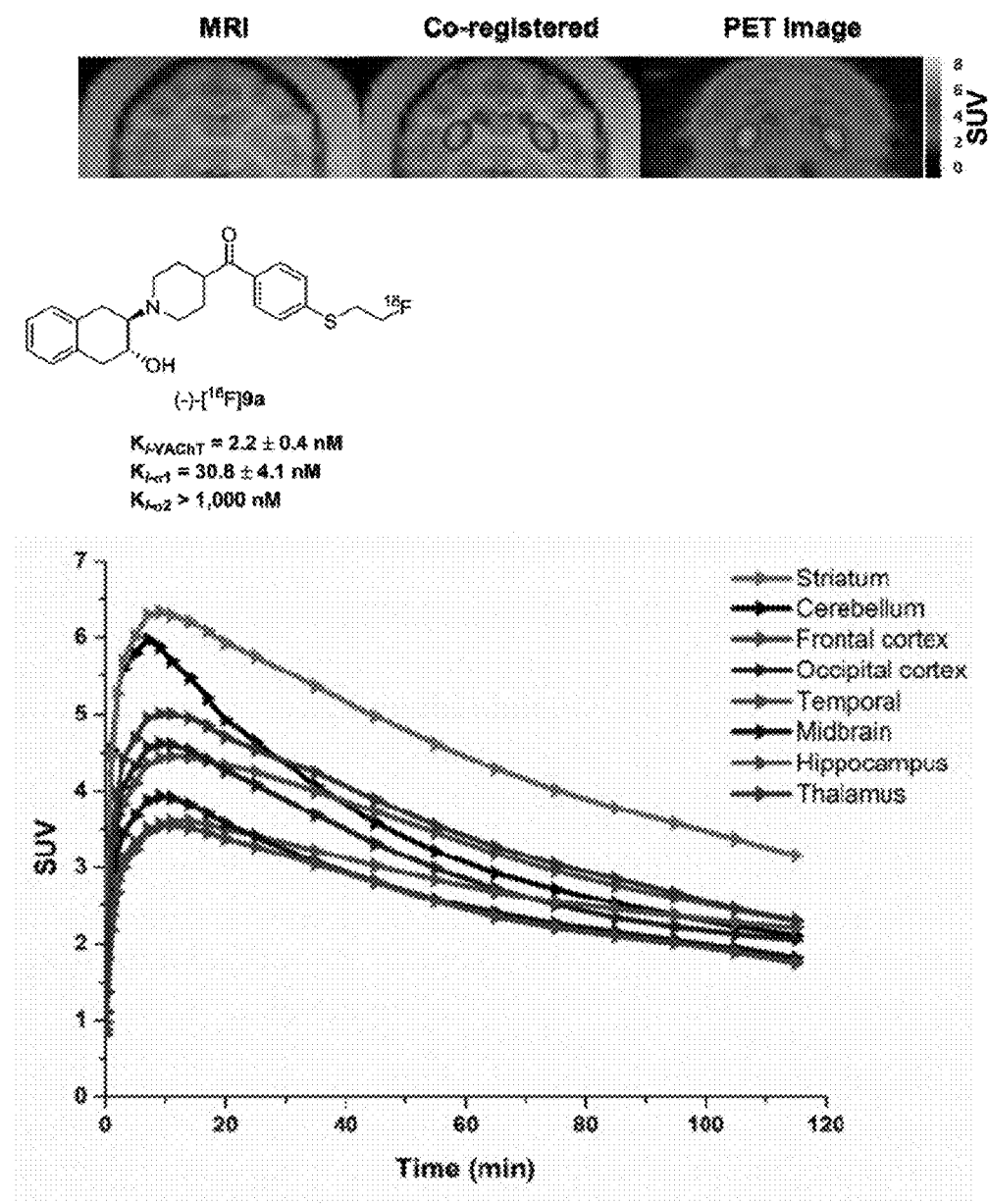
FIG. 8 is MicroPET imaging studies of (−)-[18F]9a on cynomolgus monkey: MRI image (top left), co-registered image (top middle), and MicroPET image (top right); Tissue time-activity curves of (−)-[18F]9a in cynomolgus monkey brain (bottom left).

As shown in FIG. 7, the MicroPET imaging result suggested that (−)-[$^{11}$C]3 was able to enter the NHP brain and had the highest accumulation in the striatal region. The time-activity curves indicated that the radioactivity accumulation of (−)-[$^{11}$C]3 in striatum reached maximum with a standardized uptake value (SUV) of 4.0 at 10 min. In FIG. 8, (−)-[$^{18}$F]9a was also able to enter the NHP brain and had the highest accumulation in the striatal region versus other regions including cerebellum, cortex, temporal, midbrain, hippocampus, and thalamus. The time-activity curves indicated that the radioactivity accumulation of (−)-[$^{18}$F]9a in striatum reached maximum with a SUV of 6.3 at 6 min post injection. The uptake of (−)-[$^{18}$F]9a is higher than (−)-[$^{11}$C]3. After reaching the peak, both tracers were washed out quickly compared to the previous reported tracer (−)-[$^{18}$F]FEOBV. The uptake ratio of the target (striatum) versus reference (cerebellum) increased gradually and reached >1.5-fold after 60 min post injection. This result demonstrated that the introduction of sulfur to the tracer could improve the brain kinetic property.

Example 16: Metabolite Study on NHP Plasma

The MicroPET imaging studies in NHPs, demonstrated that both (−)-[$^{11}$C]3 and (−)-[$^{18}$F]9a had favorable brain kinetic properties. In order to further understand the kinetic property, radioactive metabolite analysis on HPLC was performed for NHP plasma. (−)-[$^{18}$F]9a was chosen for this study because of the high uptake and longer half live of $^{18}$F. Arterial blood samples (1.2-1.5 mL) were collected at 2, 5, 15, 30, and 60 min post-injection of the radiotracer in a heparinized syringe. Aliquots of whole blood (1 mL) were counted in a well counter, then centrifuged to separate red blood cells from plasma. Aliquots of plasma (400 μL) were deproteinated using ice-cold methanol (0.92 mL) and separated by centrifugation. The solvent extract was then injected onto HPLC to identify the percentage of radioactive parent compound versus any radiolabeled metabolites. The HPLC system consisted of an Agilent SB C-18 analytic HPLC column (250 mm×4.6 mm) and an UV detector with wavelength set at 254 nm. The mobile phase was 43% acetonitrile in 0.1 M ammonium formate buffer (pH 4.5), and the flow rate was 1.0 mL/min. The HPLC fractions were collected at 1 min intervals for 16 min; each fraction was counted by a well counter to determine the radioactivity of each collection. The results were corrected for background radiation and physical decay.

Figure 9:
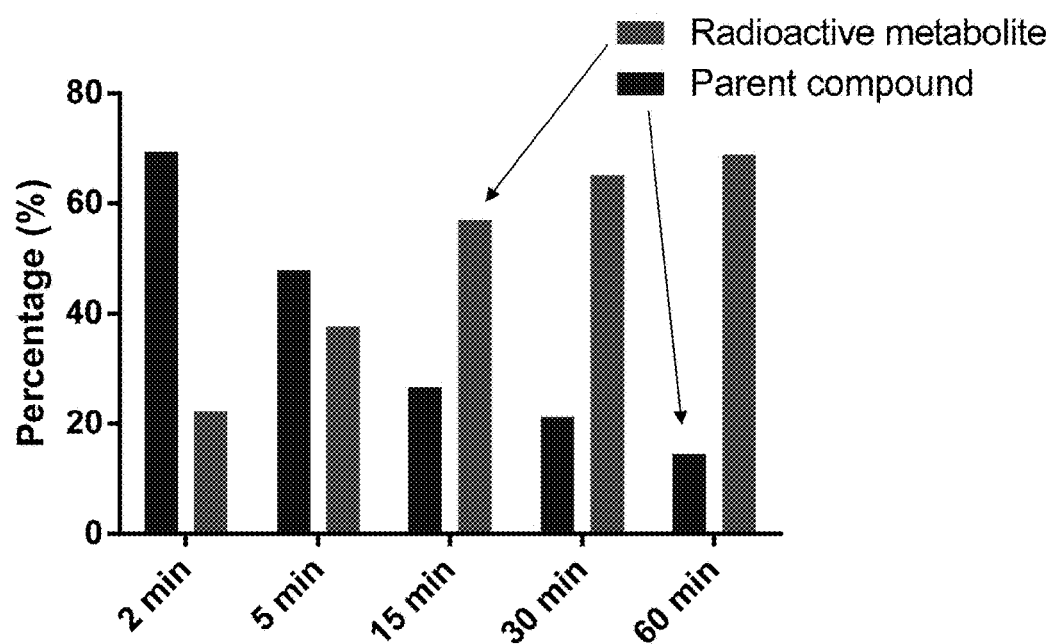
FIG. 9 is a bar graph showing radiometabolite analysis of NHP arterial plasma samples post injection of (−)-[$^{18}$F]9a. The parent compound percentage is shown as the left bar while the radioactive metabolite percentage is shown as the right bar at each time.

The HPLC metabolite analysis of the plasma samples showed two major radioactive peaks: hydrophilic radioactive metabolite ($t_R$=3-4 min) and parent compound ($t_R$=12-13 min). The percentage of the (−)-[$^{18}$F]9a was 69%, 48%, 27%, 21%, and 15% at 2 min, 5 min, 15 min, 30 min, and 60 min. The percentage of hydrophilic radioactive metabolite was increased to 70% and peaked after 30 min as shown in FIG. 9. The result indicated that (−)-[$^{18}$F]9a could be quickly metabolized in the plasma, which was consistent with the MicroPET result.

REFERENCES

1. Coyle, J., Price, D., and DeLong, M. (1983) Alzheimer's disease: a disorder of cortical cholinergic innervation. *Science* 219, 1184-1190.
2. Francis, P. T., Palmer, A. M., Snape, M., and Wilcock, G. K. (1999) The cholinergic hypothesis of Alzheimer's disease: a review of progress. *J. Neurol., Neurosurg. Psychiatry.* 66, 137-147.
3. Davies, P., and Maloney, A. J. F. (1976) Selective loss of central cholinergic neurons in Alzheimer's disease. *The Lancet* 308, 1403.
4. Bohnen, N. I., Kaufer, D. I., Ivanco, L. S., and et al. (2003) Cortical cholinergic function is more severely affected in parkinsonian dementia than in alzheimer disease: An in vivo positron emission tomographic study. *Arch. Neurol.* 60, 1745-1748.
5. Erickson, J. D., and Varoqui, H. (2000) Molecular analysis of vesicular amine transporter function and targeting to secretory organelles. *FASEB J.* 14, 2450-2458.
6. Weihe, E., Tao-Cheng, J. H., Schafer, M. K., Erickson, J. D., and Eiden, L. E. (1996) Visualization of the vesicular acetylcholine transporter in cholinergic nerve terminals and its targeting to a specific population of small synaptic vesicles. *Proc. Natl. Acad. Sci.* 93, 3547-3552.
7. Marten, M. R., Parsons, S. M., and Altar, C. A. (1987) Quantitative autoradiography of brain binding sites for the vesicular acetylcholine transport blocker 2-(4-phenylpiperidino)cyclohexanol (AH5183). *Proc. Natl. Acad. Sci. U.S.A.* 84, 876-880.
8. Roghani, A., Feldman, J., Kohan, S. A., Shirzadi, A., Gundersen, C. B., Brecha, N., and Edwards, R. H. (1994) Molecular cloning of a putative vesicular transporter for acetylcholine. *Proc. Natl. Acad. Sci. U.S.A.* 91, 10620-10624.
9. Khan, T., Sundin, A., Juhlin, C., Långström, B., Bergström, M., and Eriksson, B. (2003) $^{11}$C-metomidate PET imaging of adrenocortical cancer. *Eur. J. Nucl. Med. Mol. Imaging* 30, 403-410.
10. Luster, M., Karges, W., Zeich, K., Pauls, S., Verburg, F., Dralle, H., Glatting, G., Buck, A., Solbach, C., Neumaier, B., Reske, S., and Mottaghy, F. (2010) Clinical value of 18F-fluorodihydroxyphenylalanine positron emission tomography/computed tomography ($^{18}$F-DOPA PET/CT) for detecting pheochromocytoma. *Eur. J. Nucl. Med. Mol. Imaging* 37, 484-493.
11. Minn, H., Salonen, A., Friberg, J., Roivainen, A., Viljanen, T., Långsjö, J., Salmi, J., Välimäki, M., Någren, K., and Nuutila, P. (2004) Imaging of adrenal incidentalomas with PET using $^{11}$C-Metomidate and $^{18}$F-FDG. *J. Nucl. Med.* 45, 972-979.
12. Catafau, A. M., Searle, G. E., Bullich, S., Gunn, R. N., Rabiner, E. A., Herance, R., Radua, J., Farre, M., and Laruelle, M. (2010) Imaging cortical dopamine $D_1$ receptors using [$^{11}$C]NNC112 and ketanserin blockade of the 5-HT$_{2A}$ receptors. *J. Cereb. Blood Flow Metab.* 30, 985-993.
13. Agdeppa, E. D., Kepe, V., Liu, J., Flores-Torres, S., Satyamurthy, N., Petric, A., Cole, G. M., Small, G. W., Huang, S.-C., and Barrio, J. R. (2001) Binding characteristics of radiofluorinated 6-dialkylamino-2-naphthylethylidene derivatives as positron emission tomography imaging probes for beta-amyloid plaques in Alzheimer's disease. *J. Neurosci.* 21, 189-189.
14. Rudd, J. H., Warburton, E., Fryer, T., Jones, H., Clark, J., Antoun, N., Johnström, P., Davenport, A., Kirkpatrick, P., and Arch, B. N. (2002) Imaging atherosclerotic plaque inflammation with [$^{18}$F]-fluorodeoxyglucose positron emission tomography. *Circulation* 105, 2708-2711.
15. Gowrishankar, G., Namavari, M., Jouannot, E. B., Hoehne, A., Reeves, R., Hardy, J., and Gambhir, S. S. (2014) Investigation of 6-[$^{18}$F]-Fluoromaltose as a novel PET tracer for imaging bacterial infection. *PLoS ONE* 9, e107951.
16. Weinstein, E. A., Ordonez, A. A., DeMarco, V. P., Murawski, A. M., Pokkali, S., MacDonald, E. M., Klunk, M., Mease, R. C., Pomper, M. G., and Jain, S. K. (2014) Imaging enterobacteriaceae infection in vivo with $^{18}$F-fluorodeoxysorbitol positron emission tomography. *Sci. Transl. Med.* 6, 1-20.
17. Spencer, T. J., Biederman, J., Ciccone, P. E., Madras, B. K., Dougherty, D. D., Bonab, A. A., Livni, E., Parasrampuria, D. A., and Fischman, A. J. (2006) PET study examining pharmacokinetics, detection and likeability, and dopamine transporter receptor occupancy of short- and long-acting oral methylphenidate. *Am. J. Psychiatry* 163, 387-395.
18. Kikuchi, T., Okamura, T., Zhang, M.-R., and Irie, T. (2013) PET probes for imaging brain acetylcholinesterase. *J. Labelled Compd. Radiopharm.* 56, 172-179.
19. Widen, L., Eriksson, L., Ingvar, M., Parsons, S. M., Rogers, G. A., and Stone-Elander, S. (1992) Positron emission tomographic studies of central cholinergic nerve terminals. *Neurosci. Lett.* 136, 1-4.
20. Gage, H. D., Voytko, M. L., Ehrenkaufer, R. L. E., Tobin, J. R., Efange, S. M. N., and Mach, R. H. (2000) Reproducibility of repeated measures of cholinergic terminal density using [$^{18}$F](+) 4-Fluorobenzyltrozamicol and PET in the rhesus monkey brain. *J. Nucl. Med.* 41, 2069-2076.

21. Kilbourn, M. R., Jung, Y.-W., Haka, M. S., Gildersleeve, D. L., Kuhl, D. E., and Wieland, D. M. (1990) Mouse brain distribution of a carbon-11 labeled vesamicol derivative: Presynaptic marker of cholinergic neurons. *Life Sci.* 47, 1955-1963.
22. Petrou, M., Frey, K. A., Kilbourn, M. R., Scott, P. J. H., Raffel, D. M., Bohnen, N. I., Müller, M. L. T. M., Albin, R. L., and Koeppe, R. A. (2014) In vivo imaging of human cholinergic nerve terminals with (−)-5-[18F-Fluoroethoxy-benzovesamicol: biodistribution, dosimetry, and tracer kinetic analyses. *J. Nucl. Med.* 55, 396-404.
23. Liu, H., Jin, H., Li, J., Zhang, X., Kaneshige, K., Parsons, S. M., Perlmutter, J. S., and Tu, Z. (2015) In vitro and ex vivo characterization of (−)-TZ659 as a ligand for imaging the vesicular acetylcholine transporter. *Eur. J. Pharmacol.* 752, 18-25.
24. Yue, X., Bognar, C., Zhang, X., Gaehle, G. G., Moerlein, S. M., Perlmutter, J. S., and Tu, Z. (2016) Automated production of [$^{18}$F]VAT suitable for clinical PET study of vesicular acetylcholine transporter. *Appl. Radiat. Isot.* 107, 40-46.
25. Jin, H., Yue, X., Zhang, X., Li, J., Yang, H., Flores, H., Karimi, M., Perlmutter, J., Parsons, S., and Tu, Z. (2015) A promising F-18 labeled PET radiotracer (−)-[$^{18}$F]VAT for assessing the VAChT in vivo. *J. Nucl. Med.* 56, 4.
26. Black, S. (1963) The biochemistry of sulfur-containing compounds. *Annu. Rev. Biochem.* 32, 399-418.
27. Tu, Z., Efange, S. M. N., Xu, J., Li, S., Jones, L. A., Parsons, S. M., and Mach, R. H. (2009) Synthesis and in vitro and in vivo evaluation of $^{18}$F-labeled positron emission tomography (PET) ligands for imaging the vesicular acetylcholine transporter. *J. Med. Chem.* 52, 1358-1369.
28. Shavnya, A., Coffey, S. B., Smith, A. C., and Mascitti, V. (2013) Palladium-catalyzed sulfination of aryl and heteroaryl halides: direct access to sulfones and sulfonamides. *Org. Lett.* 15, 6226-6229.
29. Liu, Y., Kim, J., Seo, H., Park, S., and Chae, J. (2015) Copper(II)-catalyzed single-step synthesis of aryl thiols from aryl halides and 1,2-ethanedithiol. *Adv. Synth. Catal.* 357, 2205-2212.
30. Tu, Z., Zhang, X., Jin, H., Yue, X., Padakanti, P. K., Yu, L., Liu, H., Flores, H. P., Kaneshige, K., Parsons, S. M., and Perlmutter, J. S. (2015) Synthesis and biological characterization of a promising F-18 PET tracer for vesicular acetylcholine transporter. *Bioorg. Med. Chem.* 23, 4699-4709.
31. Li, J., Zhang, X., Zhang, Z., Padakanti, P. K., Jin, H., Cui, J., Li, A., Zeng, D., Rath, N. P., Flores, H., Perlmutter, J. S., Parsons, S. M., and Tu, Z. (2013) Heteroaromatic and aniline derivatives of piperidines as potent ligands for vesicular acetylcholine transporter. *J. Med. Chem.* 56, 6216-6233.
32. Zea-Ponce, Y., Mavel, S., Assaad, T., Kruse, S. E., Parsons, S. M., Emond, P., Chalon, S., Giboureau, N., Kassiou, M., and Guilloteau, D. (2005) Synthesis and in vitro evaluation of new benzovesamicol analogues as potential imaging probes for the vesicular acetylcholine transporter. *Bioorg. Med. Chem.* 13, 745-753.
33. Tu, Z., Dence, C. S., Ponde, D. E., Jones, L., Wheeler, K. T., Welch, M. J., and Mach, R. H. (2005) Carbon-11 labeled $\sigma_2$ receptor ligands for imaging breast cancer. *Nucl. Med. Biol.* 32, 423-430.
34. Tu, Z., Xu, J., Jones, L. A., Li, S., Dumstorff, C., Vangveravong, S., Chen, D. L., Wheeler, K. T., Welch, M. J., and Mach, R. H. (2007) Fluorine-18-labeled benzamide analogues for imaging the $\sigma_2$ receptor status of solid tumors with positron emission tomography. *J. Med. Chem.* 50, 3194-3204.
35. Yung-Chi, C., and Prusoff, W. H. (1973) Relationship between the inhibition constant ($K_I$) and the concentration of inhibitor which causes 50 percent inhibition ($I_{50}$) of an enzymatic reaction. *Biochem. Pharmacol.* 22, 3099-3108.

What is claimed is:
1. A compound having a structure of Formula I, or a salt thereof:

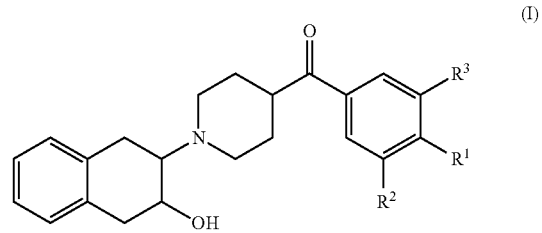

(I)

wherein $R^1$, $R^2$, and $R^3$ are each independently hydrogen, $C_1$-$C_6$ alkyl, or

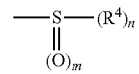

and at least one of $R^1$, $R^2$, and $R^3$ is

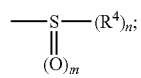

$R^4$ is a substituted or unsubstituted $C_1$-$C_6$ alkyl; substituted or unsubstituted amino;
m is 0, 1 or 2; and
n is 0 or 1.
2. The compound of claim 1 wherein at least two of $R^1$, $R^2$, and $R^3$ are hydrogen.
3. The compound of claim 1 wherein $R^2$ and $R^3$ are each hydrogen.
4. The compound of claim 1 wherein $R^4$ is a $C_1$-$C_6$ alkyl, substituted or unsubstituted $C_1$-$C_6$ alkylamino, substituted or unsubstituted $C_1$-$C_6$ haloalkyl.
5. The compound of claim 1 wherein $R^4$ is a methyl, ethyl, propyl, butyl, fluoroethyl, fluoropropyl, methylamino, ethylamino, fluoroethylamino, or fluoropropylamino.
6. The compound of claim 1 wherein Formula I has the structure of Formula II, or salt thereof:

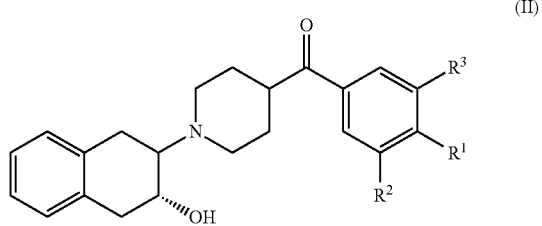

(II)

wherein $R^1$, $R^2$, and $R^3$ are as defined above.

7. The compound of claim 1 wherein Formula I has a structure selected from the group consisting of:

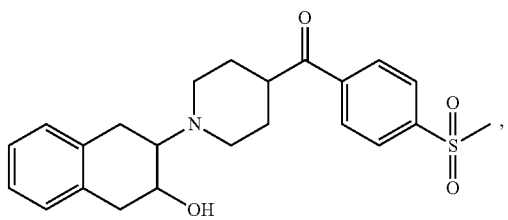

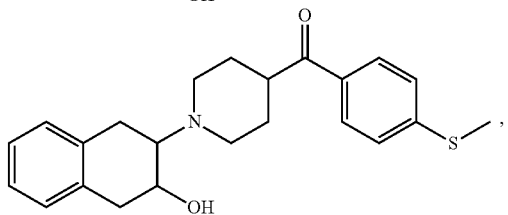

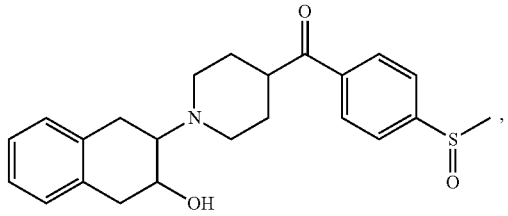

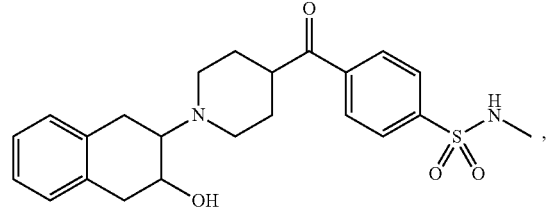

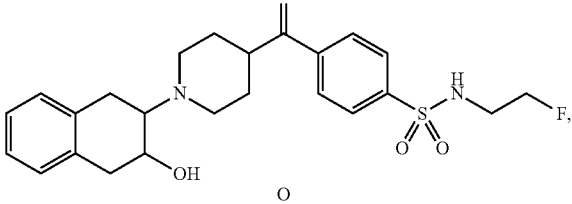

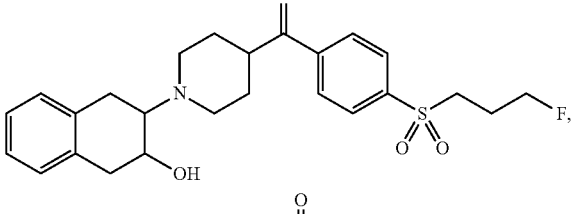

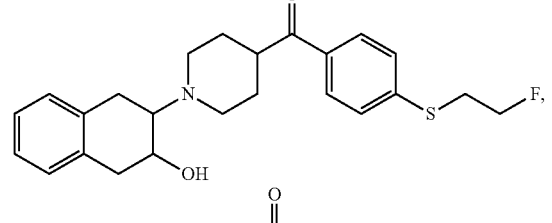

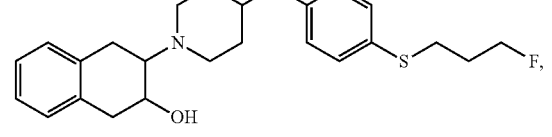

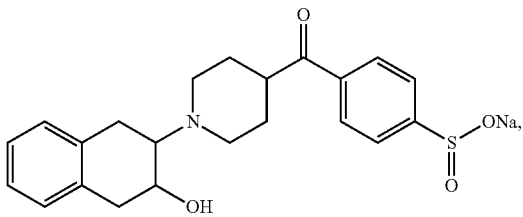

stereoisomers or salts thereof, and mixtures thereof.

8. The compound of claim 1 wherein Formula I has a structure selected from the group consisting of:

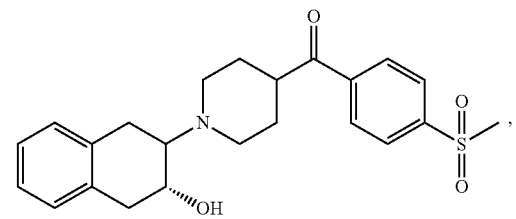

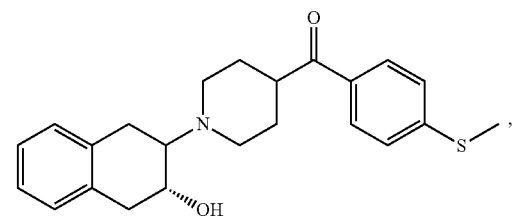

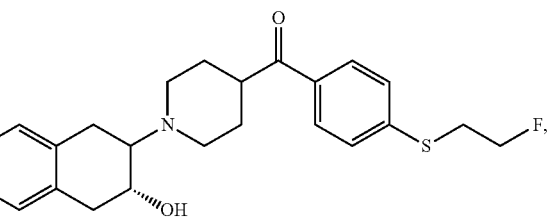

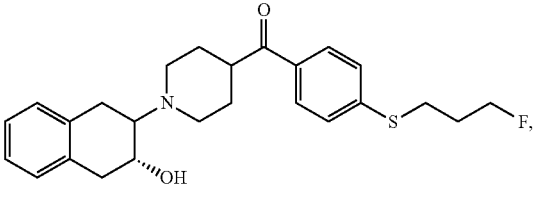

stereoisomers or salts thereof, and mixtures thereof.

9. The compound of claim 1 wherein Formula I has a structure selected from the group consisting of:

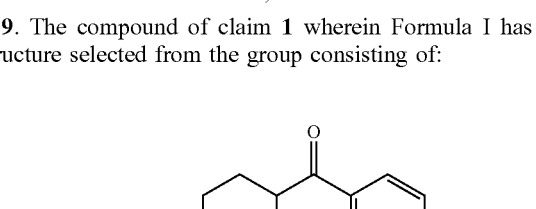

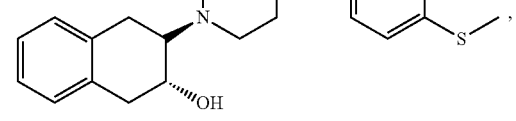

-continued

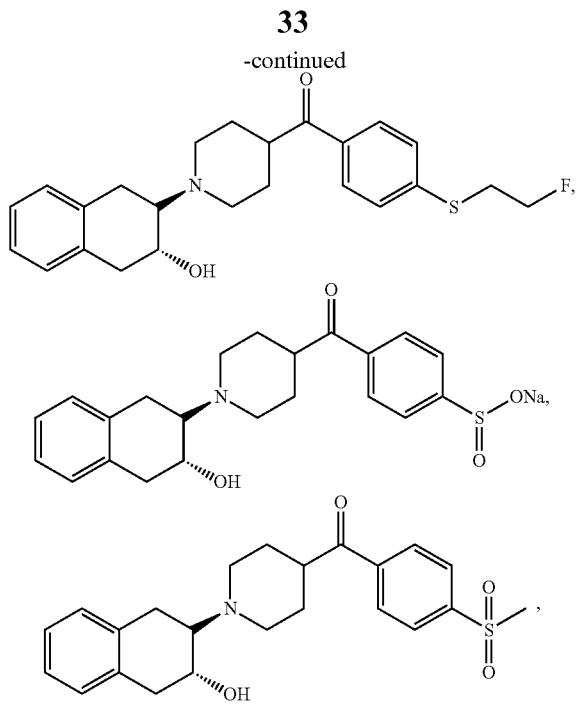

salts thereof, and mixtures thereof.

10. The compound of claim 1 wherein the compound is radiolabeled with a synthetic radioactive isotope.

11. The compound of claim 10 wherein the synthetic radioactive isotope is selected from the group consisting of carbon-11, nitrogen-13, oxygen-15, fluorine-18, bromine-76, iodine-123, and iodine-125.

12. The compound of claim 11 wherein the radiolabeled compound is selected from a group consisting of:

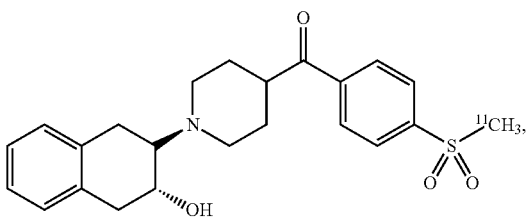

-continued

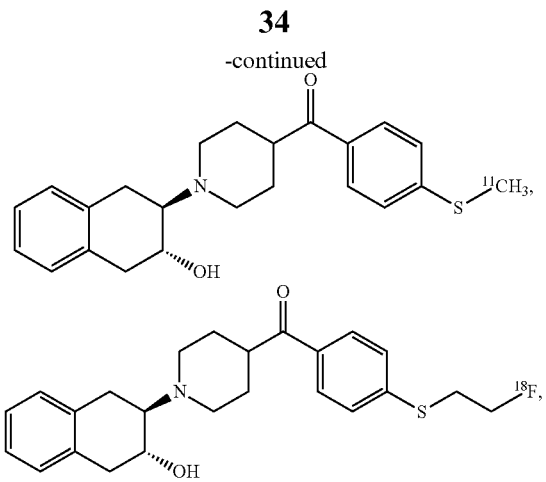

salts thereof, and mixtures thereof.

13. A pharmaceutical composition comprising a radiolabeled compound of claim 10.

14. A pharmaceutical composition comprising a compound of claim 10 wherein the composition comprises from about 0.001 mg to about 10 g of the compound and at least about 10 wt. %, at least about 25 wt. %, at least about 50 wt. %, at least about 75 wt. %, at least about 90 wt. %, or at least about 95 wt. % of the compound in the pharmaceutical composition is radiolabeled.

15. A method of diagnosing or monitoring a neurodegenerative disease in a mammal comprising administering a composition comprising a compound of claim 10 to the mammal; and imaging the mammal's brain by positron emission tomography.

16. A method of quantifying vesicular acetylcholine transporter (VAChT) in a mammal comprising administering a composition comprising a compound of claim 10 to the mammal; and imaging the mammal's brain by positron emission tomography.

17. The method of claim 15 wherein the neurodegenerative disease comprises Parkinson's Disease or Alzheimer's Disease.

18. The method of claim 15 wherein the mammal is a human.

19. The method of claim 17 wherein the mammal is a human.

20. The method of claim 16 wherein the mammal is a human.

* * * * *